US012187815B2

(12) United States Patent
Sharma

(10) Patent No.: US 12,187,815 B2
(45) Date of Patent: *Jan. 7, 2025

(54) ANTI-INFLAMMATORY NANOFIBERS

(71) Applicant: NORTHWESTERN UNIVERSITY, Evanston, IL (US)

(72) Inventor: Arun K. Sharma, Elmwood Park, IL (US)

(73) Assignee: Northwestern University, Evanston, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 17/517,063

(22) Filed: Nov. 2, 2021

(65) Prior Publication Data
US 2022/0048952 A1 Feb. 17, 2022

Related U.S. Application Data

(63) Continuation of application No. 16/192,384, filed on Nov. 15, 2018, now Pat. No. 11,161,876, which is a continuation of application No. 15/239,234, filed on Aug. 17, 2016, now abandoned.

(60) Provisional application No. 62/206,090, filed on Aug. 17, 2015.

(51) Int. Cl.
C07K 7/08 (2006.01)
A61K 38/00 (2006.01)
A61P 13/00 (2006.01)
C07K 7/06 (2006.01)

(52) U.S. Cl.
CPC ............... C07K 7/08 (2013.01); A61K 38/00 (2013.01); A61P 13/00 (2018.01); C07K 7/06 (2013.01); C07K 2319/735 (2013.01)

(58) Field of Classification Search
CPC ...... C07K 7/08; C07K 7/06; C07K 2319/735; A61K 38/00; A61P 13/00
See application file for complete search history.

(56) References Cited

U.S. PATENT DOCUMENTS

| | | | |
|---|---|---|---|
| 5,645,860 A | 7/1997 | Knapp et al. | |
| 6,890,654 B2 | 5/2005 | Stupp et al. | |
| 7,371,719 B2 | 5/2008 | Stupp et al. | |
| 7,390,526 B2 | 6/2008 | Stupp et al. | |
| 7,452,679 B2 | 11/2008 | Stupp et al. | |
| 7,491,690 B2 | 2/2009 | Stupp et al. | |
| 7,534,761 B1 | 5/2009 | Stupp et al. | |
| 7,544,661 B2 | 6/2009 | Stupp et al. | |
| 7,554,021 B2 | 6/2009 | Stupp et al. | |
| 7,579,189 B2 | 8/2009 | Freyman et al. | |
| 7,683,025 B2 | 3/2010 | Stupp et al. | |
| 7,745,708 B2 | 6/2010 | Stupp et al. | |
| 7,838,491 B2 | 11/2010 | Stupp et al. | |
| 7,851,445 B2 | 12/2010 | Stupp et al. | |
| 8,063,014 B2 | 11/2011 | Stupp et al. | |
| 8,080,262 B2 | 12/2011 | Lee et al. | |
| 8,114,834 B2 | 2/2012 | Hsu et al. | |
| 8,114,835 B2 | 2/2012 | Mata et al. | |
| 8,124,583 B2 | 2/2012 | Stupp et al. | |
| 8,138,140 B2 | 3/2012 | Stupp et al. | |
| 8,450,271 B2 | 5/2013 | Shah et al. | |
| 8,512,693 B2 | 8/2013 | Capito et al. | |
| 11,161,876 B2 | 11/2021 | Sharma et al. | |
| 2010/0316614 A1 | 12/2010 | Sharma et al. | |
| 2012/0294902 A1 | 11/2012 | Stupp et al. | |
| 2017/0051016 A1 | 2/2017 | Sharma et al. | |

FOREIGN PATENT DOCUMENTS

| | | | | |
|---|---|---|---|---|
| WO | WO-02085927 A1 | * | 10/2002 | ........... C07K 14/811 |
| WO | WO 2003/007879 | | 1/2003 | |
| WO | WO 2010/054013 | | 5/2010 | |

OTHER PUBLICATIONS

Ashley et al., Leukocyte inflammatory response in a rat urinary bladder regeneration model using porcine small intestinal submucosa scaffold. Tissue Eng Part A. Nov. 2009;15(11):3241-6.
Ashley et al., Regional variations in small intestinal submucosa evoke differences in inflammation with subsequent impact on tissue regeneration in the rat bladder augmentation model. BJU Int. May 2010;105(10):1462-8.
Azouz et al., Immunoinflammatory responses and fibrogenesis. Med Electron Microsc. Sep. 2004;37(3):141-8.
Bongartz et al., Anti-TNF antibody therapy in rheumatoid arthritis and the risk of serious infections and malignancies: systematic review and meta-analysis of rare harmful effects in randomized controlled trials. JAMA. May 17, 2006;295(19):2275-85.
Caione et al., In vivo bladder regeneration using small intestinal submucosa: experimental study. Pediatr Surg Int. Jul. 2006;22(7):593-9.
Chen et al., Decreasing TNF-alpha results in less fibrosis and earlier resolution of granulomatous experimental autoimmune thyroiditis. J Leukoc Biol. Jan. 2007;81(1):306-14.
Cui et al., N-acetylcysteine inhibits TNF-alpha, sTNFR, and TGF-beta1 release by alveolar macrophages in idiopathic pulmonary fibrosis in vitro. Sarcoidosis Vasc Diffuse Lung Dis. Jul. 2009;26(2):147-54.
Diegelmann et al., Wound healing: an overview of acute, fibrotic and delayed healing. Front Biosci. Jan. 1, 2004;9:283-9.
Frangogiannis et al., The inflammatory response in myocardial infarction. Cardiovasc Res. Jan. 2002;53(1):31-47.
Gerridzen et al., Risk factors for upper tract deterioration in chronic spinal cord injury patients. J Urol. Feb. 1992;147(2):416-8.
Gurtner et al., Wound repair and regeneration. Nature. May 15, 2008;453(7193):314-21.

(Continued)

Primary Examiner — James H Alstrum-Acevedo
Assistant Examiner — Erinne R Dabkowski
(74) Attorney, Agent, or Firm — David W. Staple; Casimir Jones, S.C.

(57) ABSTRACT

Provided herein are anti-inflammatory nanofibers and methods of use thereof. In particular methods are provided for the use of anti-inflammatory nanofibers in the promotion of tissue (e.g., urinary bladder tissue) regeneration.

5 Claims, 25 Drawing Sheets
Specification includes a Sequence Listing.

(56) References Cited

OTHER PUBLICATIONS

Hamid et al., Comparison of biochemistry and diet in patients with enterocystoplasty who do and do not form stones. BJU Int. Jun. 2008;101(11):1427-32.

Hartgerink et al., Self-assembly and mineralization of peptide-amphiphile nanofibers. Science. Nov. 23, 2001;294(5547):1684-8.

Kim et al., Expression of monocyte chemoattractant protein-1 and macrophage inflammatory protein-1 in porcine circovirus 2-induced granulomatous inflammation. J Comp Pathol. Aug.-Oct. 2004;131(2-3):121-6.

Mantovani et al., Macrophage plasticity and polarization in tissue repair and remodelling. J Pathol. Jan. 2013;229(2):176-85.

Moon et al., Synthetic RGDS peptide attenuates lipopolysaccharide-induced pulmonary inflammation by inhibiting integrin signaled MAP kinase pathways. Respir Res. Mar. 9, 2009;10:18.

Oberpenning et al., De novo reconstitution of a functional mammalian urinary bladder by tissue engineering. Nat Biotechnol. Feb. 1999;17(2):149-55.

Park et al., Understanding of the role of immune regulation in wound healing. Am J Surg. May 2004;187(5A):11S-16S.

Ryden et al., Early inflammatory response in soft tissues induced by thin calcium phosphates. J Biomed Mater Res A. Sep. 2013;101(9):2712-7.

Serhan et al., Resolution of inflammation: the beginning programs the end. Nat Immunol. Dec. 2005;6(12):1191-7.

Sharma et al., A nonhuman primate model for urinary bladder regeneration using autologous sources of bone marrow-derived mesenchymal stem cells. Stem Cells. Feb. 2011;29(2):241-50.

Silva et al., Selective differentiation of neural progenitor cells by high-epitope density nanofibers. Science. Feb. 27, 2004;303(5662):1352-5.

Slaughenhoupt et al., A large animal model of bladder exstrophy: observations of bladder smooth muscle and collagen content. J Urol. Dec. 1999;162(6):2119-22.

Tang et al., Inflammatory responses to biomaterials. Am J Clin Pathol. Apr. 1995;103(4):466-71.

Tang et al., Regulatory T cells ameliorate cardiac remodeling after myocardial infarction. Basic Res Cardiol. Jan. 2012;107(1):232.

Velnar et al., The wound healing process: an overview of the cellular and molecular mechanisms. J Int Med Res. 2009;37;1528-42.

Zhang et al., Enhanced IL-1 beta and tumor necrosis factor-alpha release and messenger RNA expression in macrophages from idiopathic pulmonary fibrosis or after asbestos exposure. J Immunol 1993;150;4188-96.

Zuo et al., A paracrine mechanism involving renal tubular cells, adipocytes and macrophages promotes kidney stone formation in a simulated metabolic syndrome environment. J Urol. Jun. 2014;191(6):1906-12.

Bladder Stones: Medline Plus. National Library of Medicine. nlm.nih.gov/medlineplus/ency/article/001275.htm. Retrieved Oct. 26, 2017. 3 pages.

Calderon et al., A humanized mouse model of tuberculosis. PLoS One. May 17, 2013;8(5):e63331.

Datta et al., Novel therapeutic approaches for pulmonary fibrosis. Br J Pharmacol. May 2011;163(1):141-72.

Deng et al., cell CD37 deficiency enables multiorgan tissue inflammation. J Immunol. Oct. 1, 2013;191(7):3563-7.

Dinarello et al., Treating inflammation by blocking interleukin-1 in humans. Semin Immunol. Dec. 15, 2013;25(6):469-84.

Fujii et al., Mouse model of carbon tetrachloride induced liver fibrosis: Histopathological changes and expression of CD133 and epidermal growth factor. BMC Gastroenterol 2010;10:79-89.

Galli et al., Phenotypic and functional plasticity of cells of innate immunity: macrophages, mast cells and neutrophils. Nat Immunol. Oct. 19, 2011;12(11):1035-44.

Gessner et al., Mast cells, basophils, and eosinophils acquire constitutive IL-4 and IL-13 transcripts during lineage differentiation that are sufficient for rapid cytokine production. J Immunol. Jan. 15, 2005;174(2):1063-72.

Grover et al., Role of inflammation in bladder function and interstitial cystitis. Ther Adv Urol. Feb. 2011;3(1):19-33.

Hawkes et al., Selective targeting of perivascular macrophages for clearance of beta-amyloid in cerebral amyloid angiopathy. Proc Natl Acad Sci U S A. Jan. 27, 2009;106(4):1261-6.

Hazen et al., Human neutrophils employ the myeloperoxidase-hydrogen peroxide-chloride system to oxidize alpha-amino acids to a family of reactive aldehydes. Mechanistic studies identifying labile intermediates along the reaction pathway. J Biol Chem. Feb. 27, 1998;273(9):4997-5005.

Inoue et al., T cells down-regulate macrophage TNF production by IRAK1-mediated IL-10 expression and control innate hyperinflammation. Proc Natl Acad Sci U S A. Apr. 8, 2014;111(14):5295-300.

Kempf et al., CD68+ cells of monocyte/macrophage lineage in the environment of AIDS-associated and classic-sporadic Kaposi sarcoma are singly or doubly infected with human herpesviruses 7 and 6B. Proc Natl Acad Sci U S A. Jul. 8, 1997;94(14):7600-5.

Khare et al., The PYRIN domain-only protein POP3 inhibits ALR inflammasomes and regulates responses to infection with DNA viruses. Nat Immunol. Apr. 2014;15(4):343-53.

Kigerl et al., Identification of two distinct macrophage subsets with divergent effects causing either neurotoxicity or regeneration in the injured mouse spinal cord. J Neurosci. Oct. 28, 2009;29(43):13435-44.

Lekstrom-Himes et al., Inhibition of human neutrophil IL-8 production by hydrogen peroxide and dysregulation in chronic granulomatous disease. J Immunol. Jan. 1, 2005;174(1):411-7.

Malik et al., Inflammasome components Asc and caspase-1 mediate biomaterial-induced inflammation and foreign body response. Proc Natl Acad Sci U S A. Dec. 13, 2011;108(50):20095-100.

Mayo et al. A recipe for designing water-soluble, beta-sheet-forming peptides. Protein Sci. Jul. 1996;5(7):1301-15.

Montesano et al., Transforming growth factor beta stimulates collagen-matrix contraction by fibroblasts: implications for wound healing. Proc Natl Acad Sci U S A. Jul. 1988;85(13):4894-7.

Murray, The primary mechanism of the IL-10-regulated antiinflammatory response is to selectively inhibit transcription. Proc Natl Acad Sci U S A. Jun. 14, 2005;102(24):8686-91.

Roupé et al., Injury is a major inducer of epidermal innate immune responses during wound healing. J Invest Dermatol. Apr. 2010; 130(4):1167-77.

Sharma et al., Cotransplantation with specific populations of spina bifida bone marrow stem/progenitor cells enhances urinary bladder regeneration. Proc Natl Acad Sci U S A. Mar. 5, 2013;110(10):4003-8.

Sharma et al., Urinary bladder smooth muscle regeneration utilizing bone marrow derived mesenchymal stem cell seeded elastomeric poly(1,8-octanediol-co-citrate) based thin films. Biomaterials. Aug. 2010;31(24):6207-17.

Sohn et al., Novel transglutaminase inhibitors reverse the inflammation of allergic conjunctivitis. J Clin Invest. Jan. 2003;111(1):121-8.

Souza et al., Interaction between pro-inflammatory and anti-inflammatory cytokines in insulin-producing cells. J Endocrinol. Apr. 2008;197(1):139-50.

Ten Broek et al., Burden of adhesions in abdominal and pelvic surgery: systematic review and met-analysis. BMJ. Oct. 3, 2013;347:f5588.

Tili et al., Mutator activity induced by microRNA-155 (miR-155) links inflammation and cancer. Proc Natl Acad Sci U S A. Mar. 22, 2011;108(12):4908-13.

Vacanti et al., Localized delivery of dexamethasone from electrospun fibers reduces the foreign body response. Biomacromolecules. J Int Med Res. Sep.-Oct. 2009;37(5):1528-42.

Webber et al., Supramolecular nanostructures that mimic VEGF as a strategy for ischemic tissue repair. Proc Natl Acad Sci U S A. Aug. 16, 2011;108(33):13438-43.

Webber et al., Development of bioactive peptide amphiphiles for therapeutic cell delivery. Acta Biomater. Jan. 2010;6(1):3-11.

Webber et al., Controlled release of dexamethasone from peptide nanofiber gels to modulate inflammatory response. Biomaterials. Oct. 2012;33(28):6823-32.

(56) References Cited

OTHER PUBLICATIONS

Wynn, Common and unique mechanisms regulate fibrosis in various fibroproliferative diseases. J Clin Invest. Mar. 2007;117(3):524-9.

* cited by examiner

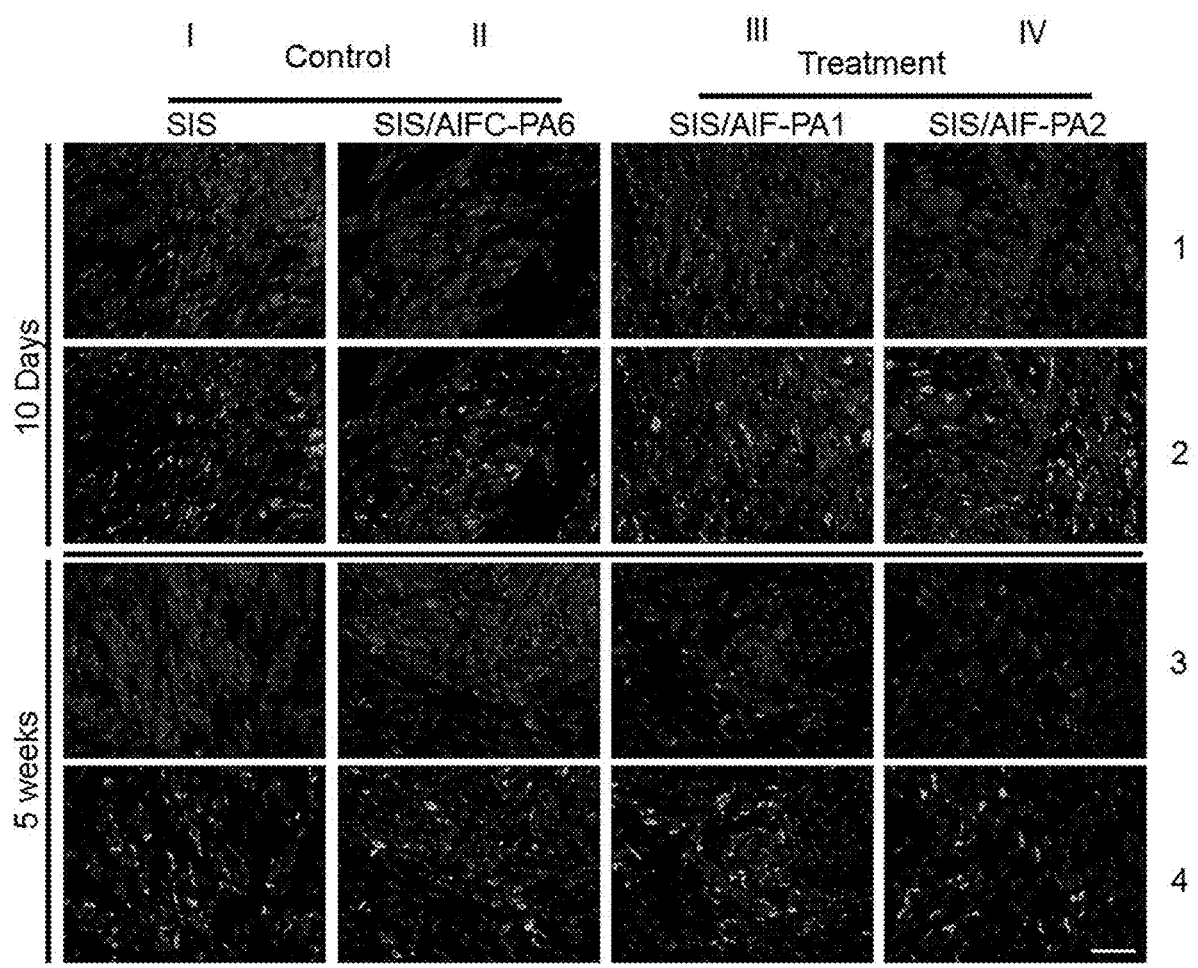

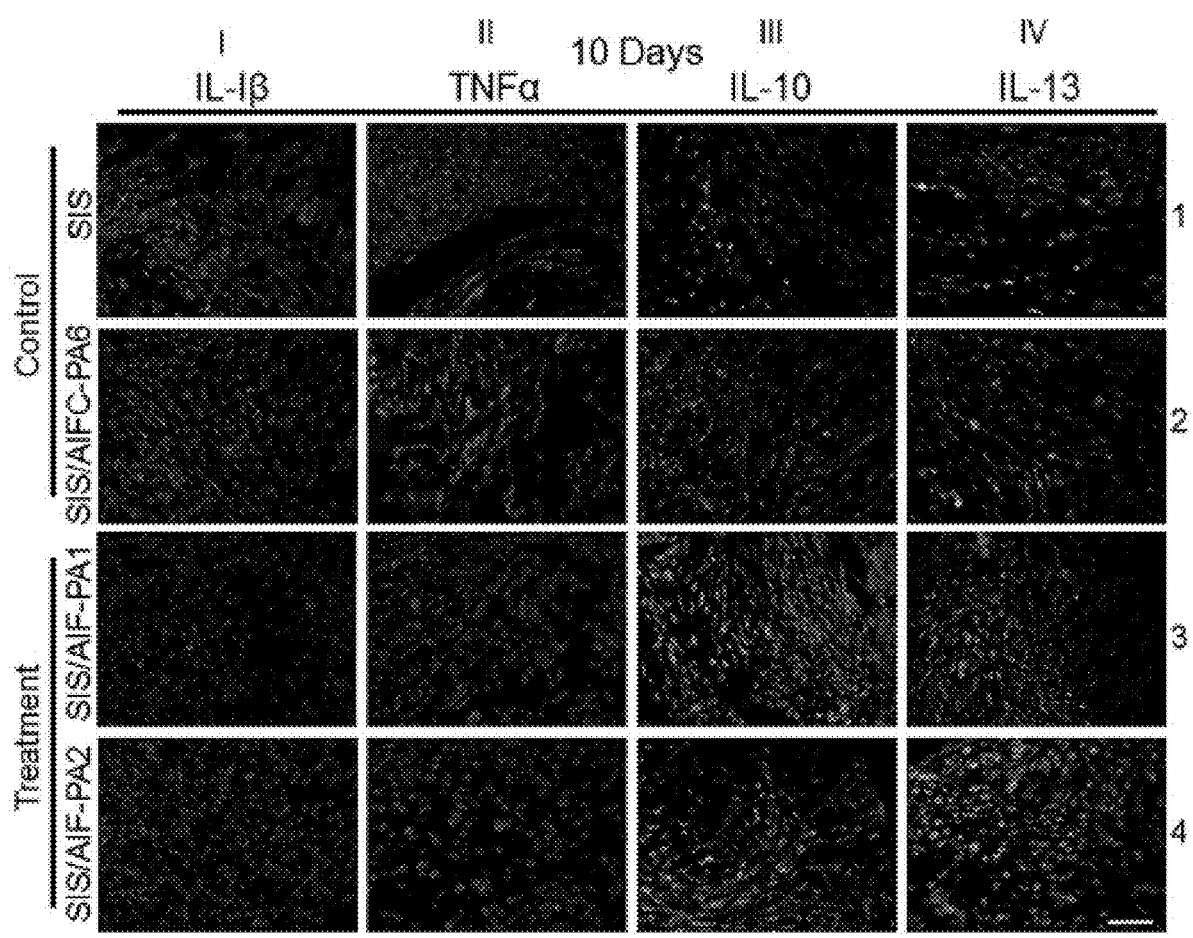

FIG. 4B

| Cytokine expression (shown as percentage of cells staining positive) | | Pro-inflammatory | | | Anti-inflammatory | |
|---|---|---|---|---|---|---|
| | | IL-1β | TNFα | | IL-10 | IL-13 |
| Control | SIS | 56.7 ± 5.0 | 63.1 ± 2.6 | | 22.0 ± 2.6 | 24.8 ± 2.5 |
| | SIS/AIFC-PA6 | 63.3 ± 2.4 | 65.1 ± 5.1 | | 27.8 ± 3.0 | 28.6 ± 3.0 |
| Treatment | SIS/AIF-PA1 | 28.2 ± 2.4 ** / *** | 32.8 ± 2.5 ** / ** | | 52.0 ± 3.1 ** / ** | 48.2 ± 2.8 ** / ** |
| | SIS/AIF-PA2 | 21.2 ± 2.4 *** / *** | 26.3 ± 2.5 *** / *** | | 56.2 ± 3.4 ** / * | 41.2 ± 2.2 * / n.s. |

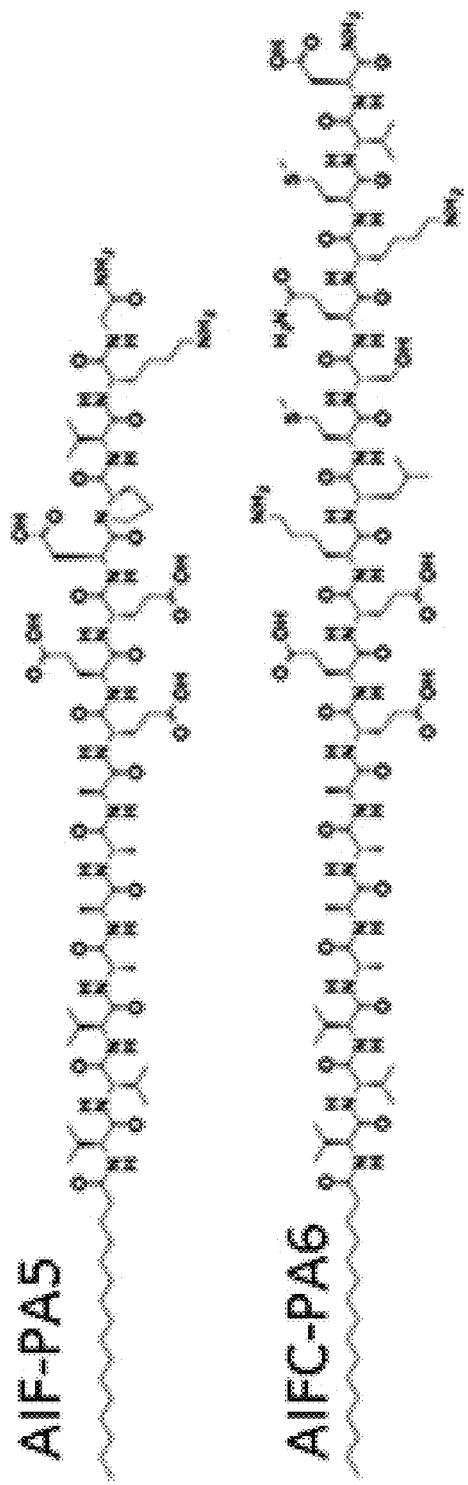

FIG. 15

|  |  | Collagen quantification (percent blue, indicating collagen) | Vasculature quantification (vessels/mm²) |
|---|---|---|---|
| 10D | Control | SIS: 73.9±0.2 | 38.5±3.8 |
|  |  | SIS/AIFC-PA6: 71.5±1.4 | 37.0±2.3 |
|  |  | SIS/AIF-PA1: 59.1±1.1 | 71.0±1.5 |
|  |  | SIS/AIF-PA2: 58.6±0.4 | 71.5±6.7 |
|  | Treatment | SIS/AIF-PA3: 60.6±0.3 <br> ** / ** | 54.9±2.7 <br> * / * |
|  |  | SIS/AIF-PA4: 63.9±2.0 <br> * / * | 53.9±2.7 <br> * / * |
|  |  | SIS/AIF-PA5: 67.3±1.6 <br> n.s. / n.s. | 43.3±2.7 <br> n.s. / n.s. |
| 5W | Control | SIS: 69.8±3.0 | 60.2±8.5 |
|  |  | SIS/AIFC-PA6: 68.8±2.7 | 53.3±4.4 |
|  | Treatment | SIS/AIF-PA1: 55.0±1.2 | 90.7±4.5 |
|  |  | SIS/AIF-PA2: 58.0±0.6 | 96.7±4.4 |

FIG. 16

Inflammatory marker expression
(shown as percentage of cells staining positive)

| | | | CD68 | Myeloperoxidase |
|---|---|---|---|---|
| 10D | Control | SIS | 66.9±2.4 | 23.1±1.8 |
| | | SIS/AIFC-PA6 | 66.5±2.4 | 22.1±1.6 |
| | | SIS/AIF-PA1 | 33.4±2.0 | 6.9±0.7 |
| | | SIS/AIF-PA2 | 23.1±3.3 | 9.0±0.5 |
| | Treatment | SIS/AIF-PA3 | 34.3±3.4 <br> */* | 10.7±0.5 <br> */* |
| | | SIS/AIF-PA4 | 37.2±2.2 <br> */* | 10.9±0.7 <br> */* |
| | | SIS/AIF-PA5 | 51.5±1.2 <br> */* | 14.7±0.9 <br> / |
| 5W | Control | SIS | 46.0±3.9 | 17.6±1.0 |
| | | SIS/AIFC-PA6 | 42.0±2.6 | 17.6±1.8 |
| | Treatment | SIS/AIF-PA1 | 17.6±1.8 | 5.2±0.7 |
| | | SIS/AIF-PA2 | 16.5±1.6 | 7.2±1.1 |

SEQUENCE LISTING

```
<160> NUMBER OF SEQ ID NOS: 51

<210> SEQ ID NO 1
<211> LENGTH: 18
<212> TYPE: PRT
<213> ORGANISM: Artificial sequence
<220> FEATURE:
<223> OTHER INFORMATION: Synthetic peptide

<400> SEQUENCE: 1

Val Val Val Ala Ala Ala Glu Glu Glu Met Gln Met Lys Lys Val Leu
1               5                   10                  15

Asp Ser

<210> SEQ ID NO 2
<211> LENGTH: 18
<212> TYPE: PRT
<213> ORGANISM: Artificial sequence
<220> FEATURE:
<223> OTHER INFORMATION: Synthetic peptide

<400> SEQUENCE: 2

Val Val Val Ala Ala Ala Glu Glu Glu His Asp Met Asn Lys Val Leu
1               5                   10                  15

Asp Leu

<210> SEQ ID NO 3
<211> LENGTH: 17
<212> TYPE: PRT
<213> ORGANISM: Artificial sequence
<220> FEATURE:
<223> OTHER INFORMATION: Synthetic peptide

<400> SEQUENCE: 3

Val Val Val Ala Ala Ala Glu Glu Glu Lys Val Leu Asp Pro Val Lys
1               5                   10                  15

Gly

<210> SEQ ID NO 4
<211> LENGTH: 17
<212> TYPE: PRT
<213> ORGANISM: Artificial sequence
<220> FEATURE:
<223> OTHER INFORMATION: Synthetic peptide

<400> SEQUENCE: 4

Val Val Val Ala Ala Ala Glu Glu Glu Lys Val Leu Asp Gly Gln Asp
1               5                   10                  15

Pro

<210> SEQ ID NO 5
<211> LENGTH: 14
<212> TYPE: PRT
<213> ORGANISM: Artificial sequence
<220> FEATURE:
```

```
<223> OTHER INFORMATION: Synthetic peptide

<400> SEQUENCE: 5

Val Val Val Ala Ala Ala Glu Glu Glu Asp Pro Val Lys Gly
1               5                   10

<210> SEQ ID NO 6
<211> LENGTH: 18
<212> TYPE: PRT
<213> ORGANISM: Artificial sequence
<220> FEATURE:
<223> OTHER INFORMATION: Synthetic peptide

<400> SEQUENCE: 6

Val Val Val Ala Ala Ala Glu Glu Glu Lys Leu Met Ser Gln Lys Met
1               5                   10                  15

Val Asp

<210> SEQ ID NO 7
<211> LENGTH: 9
<212> TYPE: PRT
<213> ORGANISM: Artificial sequence
<220> FEATURE:
<223> OTHER INFORMATION: Synthetic peptide

<400> SEQUENCE: 7

Met Gln Met Lys Lys Val Leu Asp Ser
1               5

<210> SEQ ID NO 8
<211> LENGTH: 9
<212> TYPE: PRT
<213> ORGANISM: Artificial sequence
<220> FEATURE:
<223> OTHER INFORMATION: Synthetic peptide

<400> SEQUENCE: 8

His Asp Met Asn Lys Val Leu Asp Leu
1               5

<210> SEQ ID NO 9
<211> LENGTH: 8
<212> TYPE: PRT
<213> ORGANISM: Artificial sequence
<220> FEATURE:
<223> OTHER INFORMATION: Synthetic peptide

<400> SEQUENCE: 9

Lys Val Leu Asp Pro Val Lys Gly
1               5

<210> SEQ ID NO 10
<211> LENGTH: 8
<212> TYPE: PRT
<213> ORGANISM: Artificial sequence
<220> FEATURE:
<223> OTHER INFORMATION: Synthetic peptide

<400> SEQUENCE: 10

Lys Val Leu Asp Gly Gln Asp Pro
1               5

<210> SEQ ID NO 11
<211> LENGTH: 5
<212> TYPE: PRT
<213> ORGANISM: Artificial sequence
```

```
<220> FEATURE:
<223> OTHER INFORMATION: Synthetic peptide

<400> SEQUENCE: 11

Asp Pro Val Lys Gly
1               5

<210> SEQ ID NO 12
<211> LENGTH: 9
<212> TYPE: PRT
<213> ORGANISM: Artificial sequence
<220> FEATURE:
<223> OTHER INFORMATION: Synthetic peptide

<400> SEQUENCE: 12

Val Val Val Ala Ala Ala Glu Glu Glu
1               5

<210> SEQ ID NO 13
<211> LENGTH: 6
<212> TYPE: PRT
<213> ORGANISM: Artificial sequence
<220> FEATURE:
<223> OTHER INFORMATION: Synthetic peptide

<400> SEQUENCE: 13

Val Val Val Ala Ala Ala
1               5

<210> SEQ ID NO 14
<211> LENGTH: 4
<212> TYPE: PRT
<213> ORGANISM: Artificial sequence
<220> FEATURE:
<223> OTHER INFORMATION: Synthetic peptide

<400> SEQUENCE: 14

Val Val Ala Ala
1

<210> SEQ ID NO 15
<211> LENGTH: 4
<212> TYPE: PRT
<213> ORGANISM: Artificial sequence
<220> FEATURE:
<223> OTHER INFORMATION: Synthetic peptide

<400> SEQUENCE: 15

Ala Ala Val Val
1

<210> SEQ ID NO 16
<211> LENGTH: 6
<212> TYPE: PRT
<213> ORGANISM: Artificial sequence
<220> FEATURE:
<223> OTHER INFORMATION: Synthetic peptide

<400> SEQUENCE: 16

Ala Ala Ala Val Val Val
1               5

<210> SEQ ID NO 17
<211> LENGTH: 15
<212> TYPE: PRT
<213> ORGANISM: Artificial sequence
<220> FEATURE:
```

<223> OTHER INFORMATION: Synthetic peptide

<400> SEQUENCE: 17

Val Val Ala Ala Glu Glu Met Gln Met Lys Lys Val Leu Asp Ser
1               5                   10                  15

<210> SEQ ID NO 18
<211> LENGTH: 16
<212> TYPE: PRT
<213> ORGANISM: Artificial sequence
<220> FEATURE:
<223> OTHER INFORMATION: Synthetic peptide

<400> SEQUENCE: 18

Val Val Val Ala Ala Glu Glu Met Gln Met Lys Lys Val Leu Asp Ser
1               5                   10                  15

<210> SEQ ID NO 19
<211> LENGTH: 17
<212> TYPE: PRT
<213> ORGANISM: Artificial sequence
<220> FEATURE:
<223> OTHER INFORMATION: Synthetic peptide

<400> SEQUENCE: 19

Val Val Val Ala Ala Ala Glu Glu Met Gln Met Lys Lys Val Leu Asp
1               5                   10                  15

Ser

<210> SEQ ID NO 20
<211> LENGTH: 17
<212> TYPE: PRT
<213> ORGANISM: Artificial sequence
<220> FEATURE:
<223> OTHER INFORMATION: Synthetic peptide

<400> SEQUENCE: 20

Val Val Ala Ala Ala Glu Glu Glu Met Gln Met Lys Lys Val Leu Asp
1               5                   10                  15

Ser

<210> SEQ ID NO 21
<211> LENGTH: 16
<212> TYPE: PRT
<213> ORGANISM: Artificial sequence
<220> FEATURE:
<223> OTHER INFORMATION: Synthetic peptide

<400> SEQUENCE: 21

Val Val Ala Ala Glu Glu Glu Met Gln Met Lys Lys Val Leu Asp Ser
1               5                   10                  15

<210> SEQ ID NO 22
<211> LENGTH: 17
<212> TYPE: PRT
<213> ORGANISM: Artificial sequence
<220> FEATURE:
<223> OTHER INFORMATION: Synthetic peptide

<400> SEQUENCE: 22

Val Val Val Ala Ala Glu Glu Glu Met Gln Met Lys Lys Val Leu Asp
1               5                   10                  15

Ser

```
<210> SEQ ID NO 23
<211> LENGTH: 16
<212> TYPE: PRT
<213> ORGANISM: Artificial sequence
<220> FEATURE:
<223> OTHER INFORMATION: Synthetic peptide

<400> SEQUENCE: 23

Val Val Ala Ala Ala Glu Glu Met Gln Met Lys Lys Val Leu Asp Ser
1               5                   10                  15

<210> SEQ ID NO 24
<211> LENGTH: 15
<212> TYPE: PRT
<213> ORGANISM: Artificial sequence
<220> FEATURE:
<223> OTHER INFORMATION: Synthetic peptide

<400> SEQUENCE: 24

Val Val Ala Ala Glu Glu His Asp Met Asn Lys Val Leu Asp Leu
1               5                   10                  15

<210> SEQ ID NO 25
<211> LENGTH: 16
<212> TYPE: PRT
<213> ORGANISM: Artificial sequence
<220> FEATURE:
<223> OTHER INFORMATION: Synthetic peptide

<400> SEQUENCE: 25

Val Val Val Ala Ala Glu Glu His Asp Met Asn Lys Val Leu Asp Leu
1               5                   10                  15

<210> SEQ ID NO 26
<211> LENGTH: 17
<212> TYPE: PRT
<213> ORGANISM: Artificial sequence
<220> FEATURE:
<223> OTHER INFORMATION: Synthetic peptide

<400> SEQUENCE: 26

Val Val Val Ala Ala Ala Glu Glu His Asp Met Asn Lys Val Leu Asp
1               5                   10                  15

Leu

<210> SEQ ID NO 27
<211> LENGTH: 17
<212> TYPE: PRT
<213> ORGANISM: Artificial sequence
<220> FEATURE:
<223> OTHER INFORMATION: Synthetic peptide

<400> SEQUENCE: 27

Val Val Ala Ala Ala Glu Glu Glu His Asp Met Asn Lys Val Leu Asp
1               5                   10                  15

Leu

<210> SEQ ID NO 28
<211> LENGTH: 16
<212> TYPE: PRT
<213> ORGANISM: Artificial sequence
<220> FEATURE:
<223> OTHER INFORMATION: Synthetic peptide

<400> SEQUENCE: 28

Val Val Ala Ala Glu Glu Glu His Asp Met Asn Lys Val Leu Asp Leu
```

```
1               5                  10                  15
```

<210> SEQ ID NO 29
<211> LENGTH: 17
<212> TYPE: PRT
<213> ORGANISM: Artificial sequence
<220> FEATURE:
<223> OTHER INFORMATION: Synthetic peptide

<400> SEQUENCE: 29

```
Val Val Val Ala Ala Glu Glu Glu His Asp Met Asn Lys Val Leu Asp
1               5                  10                  15

Leu
```

<210> SEQ ID NO 30
<211> LENGTH: 16
<212> TYPE: PRT
<213> ORGANISM: Artificial sequence
<220> FEATURE:
<223> OTHER INFORMATION: Synthetic peptide

<400> SEQUENCE: 30

```
Val Val Ala Ala Ala Glu Glu His Asp Met Asn Lys Val Leu Asp Leu
1               5                  10                  15
```

<210> SEQ ID NO 31
<211> LENGTH: 14
<212> TYPE: PRT
<213> ORGANISM: Artificial sequence
<220> FEATURE:
<223> OTHER INFORMATION: Synthetic peptide

<400> SEQUENCE: 31

```
Val Val Ala Ala Glu Glu Lys Val Leu Asp Pro Val Lys Gly
1               5                  10
```

<210> SEQ ID NO 32
<211> LENGTH: 15
<212> TYPE: PRT
<213> ORGANISM: Artificial sequence
<220> FEATURE:
<223> OTHER INFORMATION: Synthetic peptide

<400> SEQUENCE: 32

```
Val Val Val Ala Ala Glu Glu Lys Val Leu Asp Pro Val Lys Gly
1               5                  10                  15
```

<210> SEQ ID NO 33
<211> LENGTH: 16
<212> TYPE: PRT
<213> ORGANISM: Artificial sequence
<220> FEATURE:
<223> OTHER INFORMATION: Synthetic peptide

<400> SEQUENCE: 33

```
Val Val Val Ala Ala Ala Glu Glu Lys Val Leu Asp Pro Val Lys Gly
1               5                  10                  15
```

<210> SEQ ID NO 34
<211> LENGTH: 16
<212> TYPE: PRT
<213> ORGANISM: Artificial sequence
<220> FEATURE:
<223> OTHER INFORMATION: Synthetic peptide

<400> SEQUENCE: 34

Val Val Ala Ala Ala Glu Glu Glu Lys Val Leu Asp Pro Val Lys Gly
1               5                   10                  15

<210> SEQ ID NO 35
<211> LENGTH: 15
<212> TYPE: PRT
<213> ORGANISM: Artificial sequence
<220> FEATURE:
<223> OTHER INFORMATION: Synthetic peptide

<400> SEQUENCE: 35

Val Val Ala Ala Glu Glu Glu Lys Val Leu Asp Pro Val Lys Gly
1               5                   10                  15

<210> SEQ ID NO 36
<211> LENGTH: 16
<212> TYPE: PRT
<213> ORGANISM: Artificial sequence
<220> FEATURE:
<223> OTHER INFORMATION: Synthetic peptide

<400> SEQUENCE: 36

Val Val Val Ala Ala Glu Glu Glu Lys Val Leu Asp Pro Val Lys Gly
1               5                   10                  15

<210> SEQ ID NO 37
<211> LENGTH: 15
<212> TYPE: PRT
<213> ORGANISM: Artificial sequence
<220> FEATURE:
<223> OTHER INFORMATION: Synthetic peptide

<400> SEQUENCE: 37

Val Val Ala Ala Ala Glu Glu Lys Val Leu Asp Pro Val Lys Gly
1               5                   10                  15

<210> SEQ ID NO 38
<211> LENGTH: 14
<212> TYPE: PRT
<213> ORGANISM: Artificial sequence
<220> FEATURE:
<223> OTHER INFORMATION: Synthetic peptide

<400> SEQUENCE: 38

Val Val Ala Ala Glu Glu Lys Val Leu Asp Gly Gln Asp Pro
1               5                   10

<210> SEQ ID NO 39
<211> LENGTH: 15
<212> TYPE: PRT
<213> ORGANISM: Artificial sequence
<220> FEATURE:
<223> OTHER INFORMATION: Synthetic peptide

<400> SEQUENCE: 39

Val Val Val Ala Ala Glu Glu Lys Val Leu Asp Gly Gln Asp Pro
1               5                   10                  15

<210> SEQ ID NO 40
<211> LENGTH: 16
<212> TYPE: PRT
<213> ORGANISM: Artificial sequence
<220> FEATURE:
<223> OTHER INFORMATION: Synthetic peptide

<400> SEQUENCE: 40

Val Val Val Ala Ala Ala Glu Glu Lys Val Leu Asp Gly Gln Asp Pro

```
                1               5                  10                  15
```

\<210\> SEQ ID NO 41
\<211\> LENGTH: 16
\<212\> TYPE: PRT
\<213\> ORGANISM: Artificial sequence
\<220\> FEATURE:
\<223\> OTHER INFORMATION: Synthetic peptide

\<400\> SEQUENCE: 41

```
Val Val Ala Ala Ala Glu Glu Glu Lys Val Leu Asp Gly Gln Asp Pro
1               5                  10                  15
```

\<210\> SEQ ID NO 42
\<211\> LENGTH: 15
\<212\> TYPE: PRT
\<213\> ORGANISM: Artificial sequence
\<220\> FEATURE:
\<223\> OTHER INFORMATION: Synthetic peptide

\<400\> SEQUENCE: 42

```
Val Val Ala Ala Glu Glu Glu Lys Val Leu Asp Gly Gln Asp Pro
1               5                  10                  15
```

\<210\> SEQ ID NO 43
\<211\> LENGTH: 16
\<212\> TYPE: PRT
\<213\> ORGANISM: Artificial sequence
\<220\> FEATURE:
\<223\> OTHER INFORMATION: Synthetic peptide

\<400\> SEQUENCE: 43

```
Val Val Val Ala Ala Glu Glu Glu Lys Val Leu Asp Gly Gln Asp Pro
1               5                  10                  15
```

\<210\> SEQ ID NO 44
\<211\> LENGTH: 15
\<212\> TYPE: PRT
\<213\> ORGANISM: Artificial sequence
\<220\> FEATURE:
\<223\> OTHER INFORMATION: Synthetic peptide

\<400\> SEQUENCE: 44

```
Val Val Ala Ala Ala Glu Glu Lys Val Leu Asp Gly Gln Asp Pro
1               5                  10                  15
```

\<210\> SEQ ID NO 45
\<211\> LENGTH: 11
\<212\> TYPE: PRT
\<213\> ORGANISM: Artificial sequence
\<220\> FEATURE:
\<223\> OTHER INFORMATION: Synthetic peptide

\<400\> SEQUENCE: 45

```
Val Val Ala Ala Glu Glu Asp Pro Val Lys Gly
1               5                  10
```

\<210\> SEQ ID NO 46
\<211\> LENGTH: 12
\<212\> TYPE: PRT
\<213\> ORGANISM: Artificial sequence
\<220\> FEATURE:
\<223\> OTHER INFORMATION: Synthetic peptide

\<400\> SEQUENCE: 46

```
Val Val Val Ala Ala Glu Glu Asp Pro Val Lys Gly
1               5                  10
```

```
<210> SEQ ID NO 47
<211> LENGTH: 13
<212> TYPE: PRT
<213> ORGANISM: Artificial sequence
<220> FEATURE:
<223> OTHER INFORMATION: Synthetic peptide

<400> SEQUENCE: 47

Val Val Val Ala Ala Ala Glu Glu Asp Pro Val Lys Gly
1               5                   10

<210> SEQ ID NO 48
<211> LENGTH: 13
<212> TYPE: PRT
<213> ORGANISM: Artificial sequence
<220> FEATURE:
<223> OTHER INFORMATION: Synthetic peptide

<400> SEQUENCE: 48

Val Val Ala Ala Ala Glu Glu Glu Asp Pro Val Lys Gly
1               5                   10

<210> SEQ ID NO 49
<211> LENGTH: 12
<212> TYPE: PRT
<213> ORGANISM: Artificial sequence
<220> FEATURE:
<223> OTHER INFORMATION: Synthetic peptide

<400> SEQUENCE: 49

Val Val Ala Ala Glu Glu Glu Asp Pro Val Lys Gly
1               5                   10

<210> SEQ ID NO 50
<211> LENGTH: 13
<212> TYPE: PRT
<213> ORGANISM: Artificial sequence
<220> FEATURE:
<223> OTHER INFORMATION: Synthetic peptide

<400> SEQUENCE: 50

Val Val Val Ala Ala Glu Glu Glu Asp Pro Val Lys Gly
1               5                   10

<210> SEQ ID NO 51
<211> LENGTH: 12
<212> TYPE: PRT
<213> ORGANISM: Artificial sequence
<220> FEATURE:
<223> OTHER INFORMATION: Synthetic peptide

<400> SEQUENCE: 51

Val Val Ala Ala Ala Glu Glu Asp Pro Val Lys Gly
1               5                   10
```

ANTI-INFLAMMATORY NANOFIBERS

CROSS REFERENCE TO RELATED APPLICATIONS

The present invention is a continuation of U.S. patent application Ser. No. 16/192,384, filed Nov. 15, 2018, now U.S. Pat. No. 11,161,876, which a continuation of U.S. patent application Ser. No. 15/239,234, filed Aug. 17, 2016, now abandoned, which claims the benefit of U.S. Provisional Patent Application 62/206,090, filed Aug. 17, 2015, each of which is incorporated by reference in its entirety.

SEQUENCE LISTING

The text of the computer readable sequence listing filed herewith, titled "34496-304_SEQUENCE_LISTING_ST25", created Nov. 2, 2021, having a file size of 12,087 bytes, is hereby incorporated by reference in its entirety.

FIELD

Provided herein are anti-inflammatory nanofibers and methods of use thereof. In particular methods are provided for the use of anti-inflammatory peptide amphiphile (PA) nanofibers in the promotion of tissue (e.g., urinary bladder tissue) regeneration.

BACKGROUND

The cascade of events involved in the tissue regenerative process encompasses multiple biological programs that aid in regeneration. These are non-exclusively comprised of a robust inflammatory reaction at the onset of tissue damage subsequently accompanied by architectural and physiological remodeling of tissue. Although the inflammatory response initially acts as a protective mechanism to aid in repair and regeneration, impediments to tissue healing including perturbations in the inflammatory response, are attributable to further tissue damage and subvert proper tissue remodeling. The expected outcome of inflammation in a normal setting is to provide a suitable environment in order to recapitulate native tissue in form and in function through a series of interdependently choreographed events encompassing several distinct phases (ref.1; herein incorporated by reference in its entirety).

The inflammatory response to tissue injury is in part under the control of the innate immune system. Localized tissue injury induces the onset of leukocyte invasion, edema and pain of affected tissues (ref.2; herein incorporated by reference in its entirety). The tissue infiltration of leukocytes via extravasation including macrophages, granulocytes (basophils, neutrophils, mast cells, and eosinophils) has been demonstrated within the field of tissue regeneration as well as cancer initiation and progression (refs.3,4; herein incorporated by reference in their entireties). Neutrophils and macrophages produce pro-inflammatory cytokines and chemokines such as IL-1β, IL-6, IL-8 and TNFα. Neutrophils also possess the capacity to recruit more monocytes (and ultimately macrophages) thus continuing the cyclical process of tissue damage in a dysfunctional setting (ref.5; herein incorporated by reference in its entirety). This acute inflammatory response can become chronic and eventually lead to tissue fibrosis. Abundantly fibrous tissue lacks proper physiological function as demonstrated in a number of different conditions including the formation of adhesions following surgery, idiopathic pulmonary fibrosis, and urinary bladder tissue regeneration (refs.3,6-7; herein incorporated by reference in their entireties).

SUMMARY

Provided herein are anti-inflammatory nanofibers and methods of use thereof. In particular methods are provided for the use of anti-inflammatory peptide amphiphile (PA) nanofibers in the promotion of tissue (e.g., urinary bladder tissue) regeneration.

Attempts at tissue regeneration utilizing synthetic and decellularized biologic-based materials have been met by innate immune responses in the form of a robust inflammatory reaction at the site of implantation or grafting. This ultimately leads to tissue fibrosis with direct negative impact on tissue growth, development, and function. In order to temper the innate inflammatory response, in some embodiments herein, anti-inflammatory signals were incorporated through display on self-assembling peptide nanofibers to promote tissue healing and subsequent graft compliance throughout the regenerative process.

Experiments were conducted during development of embodiments herein utilizing a urinary bladder augmentation model; a highly pro-inflammatory biologic scaffold (e.g., decellularized small intestinal submucosa) was treated with anti-inflammatory peptide amphiphiles (AIF-PAs) or control peptide amphiphiles and used for augmentation. Significant regenerative advantages of the AIF-PAs were observed including potent angiogenic responses, limited tissue collagen accumulation, and the modulation of macrophage and neutrophil responses in regenerated bladder tissue. Upon further characterization, a reduction in the levels of M2 macrophages was observed, but not in M1 macrophages in control groups, while treatment groups exhibited decreased levels of M1 macrophages and stabilized levels of M2 macrophages. Pro-inflammatory cytokine production was decreased while anti-inflammatory cytokines were up-regulated in treatment groups. This resulted in far fewer incidences of tissue granuloma and bladder stone formation. Functional urinary bladder testing revealed greater bladder compliance and similar capacities in groups treated with AIF-PAs. Data demonstrate that AIF-PAs alleviate galvanic innate immune responses and provide a highly conducive regenerative milieu applicable in a variety of clinical settings.

In some embodiments, provided herein are peptide amphiphiles comprising: (a) a hydrophobic non-peptidic segment; (b) a structural peptide segment; (c) a charged peptide segment; and (d) an anti-inflammatory peptide segment; wherein the hydrophobic non-peptidic segment is covalently attached to the N-terminus of the structural peptide segment; wherein the C-terminus of the structural peptide segment is covalently attached to the N-terminus of the charged peptide segment; and wherein the C-terminus of the charged peptide segment is covalently attached to the N-terminus of the anti-inflammatory peptide segment.

In some embodiments, provided herein are peptide amphiphiles comprising: (a) a hydrophobic non-peptidic segment; (b) a structural peptide segment; (c) a charged peptide segment; and (d) an anti-inflammatory peptide segment; wherein the hydrophobic non-peptidic segment is covalently attached to the C-terminus of the structural peptide segment; wherein the N-terminus of the structural peptide segment is covalently attached to the C-terminus of the charged peptide segment; and wherein the N-terminus of the charged peptide segment is covalently attached to the C-terminus of the anti-inflammatory peptide segment.

In some embodiments, the peptide amphiphile comprises an anti-inflammatory segment with at least 50% sequence identity with one of MQMKKVLDS (SEQ ID NO:7), HDMNKVLDL (SEQ ID NO:8), KVLDPVKG (SEQ ID NO:9), KVLDGQDP (SEQ ID NO:10), and DPVKG (SEQ ID NO:11). In some embodiments, the peptide amphiphile comprises an anti-inflammatory segment with at least 70% sequence similarity with one of MQMKKVLDS (SEQ ID NO:7), HDMNKVLDL (SEQ ID NO:8), KVLDPVKG (SEQ ID NO:9), KVLDGQDP (SEQ ID NO:10), and DPVKG (SEQ ID NO:11). In some embodiments, the hydrophobic non-peptidic segment comprises an acyl chain. In some embodiments, the acyl chain comprises $C_6$-$C_{20}$. In some embodiments, the acyl chain comprises $C_{16}$. In some embodiments, the structural peptide segment comprises a β-sheet-forming peptide segment. In some embodiments, the β-sheet-forming peptide segment comprises alanine (A) and valine (V). In some embodiments, the β-sheet-forming peptide segment comprises AV. In some embodiments, the β-sheet-forming peptide segment comprises AAVV (SEQ ID NO:15). In some embodiments, the β-sheet-forming peptide segment comprises AAAVVV (SEQ ID NO:16). In some embodiments, the charged peptide segment comprises a plurality of Lys (K), Arg (R), Glu (E) and/or Asp (D) residues. In some embodiments, the charged peptide segment comprises 2-7 amino acids in length with 50% or more amino acids selected from Lys (K), Arg (R), Glu (E) and/or Asp (D) residues. In some embodiments, the charged peptide segment comprises EE. In some embodiments, the charged peptide segment comprises EEE. In some embodiments, the peptide amphiphile comprises: (i) $(CH_2)_{10-20}$-$V_{2-3}A_{2-3}E_{2-3}$MQMKKVLDS (SEQ ID NOS:1, 17-23); (ii) $(CH_2)_{10-20}$-$V_{2-3}A_{2-3}E_{2-3}$ HDMNKVLDL (SEQ ID NOS:2, 24-30); (iii) $(CH_2)_{10-20}$-$V_{2-3}A_{2-3}E_{2-3}$ KVLDPVKG (SEQ ID NOS:3, 31-37); (iv) $(CH_2)_{10-20}$-$V_{2-3}A_{2-3}E_{2-3}$KVLDGQDP (SEQ ID NOS: 4, 38-44); or (v) $(CH_2)_{10-20}$-$V_{2-3}A_{2-3}E_{2-3}$DPVKG (SEQ ID NOS:5, 45-51).

In some embodiments, provided herein are nanofibers comprising a peptide amphiphile herein.

In some embodiments, provided herein are methods of promoting tissue regeneration (e.g., bladder tissue) in a subject comprising administering a peptide amphiphile pr nanofiber described herein.

BRIEF DESCRIPTION OF THE DRAWINGS

FIG. 3A-C shows M1 and M2 macrophage characterization. (A) Dense populations of CD86+ M1 macrophages were visualized at both time-points post-augmentation throughout the grafted area. This was accompanied by depressed levels of CD206+M2 macrophages of the control groups, most notably at 5 W. Treatment groups saw a significant reduction in CD86+M1 macrophage presence at 5 W coupled with sustained expression of CD206+M2 macrophages along the entirety of the graft. AIF-PA2 appeared to have a greater impact on macrophage populations than AIF-PA1. Magnification is 400× (scale bar, 50 μm). (B) M1+ macrophages persisted at high levels in control groups while the SIS/AIF-PA1 treatment group demonstrated a significant decline over time. Data shown as means±SE. Significance shown for comparison of SIS/AIF-PA1 and SIS/AIF-PA2 to SIS (top) and SIS/AIFC-PA6 (bottom);**$P < 0.0001$, *$P < 0.001$, $P < 0.01$. (C) A general decrease in levels of M2+ macrophages was seen in both control and treatment groups at both time-points but M2+ macrophages were still abundant in treatment groups. Data shown as means±SE. Significance shown for comparison of SIS/AIF-PA1 and SIS/AIF-PA2 to SIS (top) and SIS/AIFC-PA6 (bottom);$P < 0.0001$, $P < 0.01$, *$P < 0.05$.

FIG. 4A-B shows pro- and anti-inflammatory cytokine expression. (A) 10D bladder tissue staining with antibodies against the pro-inflammatory cytokines IL-1β and TNFα (columns I and II) demonstrated high levels of expression in control groups but a significant reduction in treatment groups. Conversely, elevated levels of anti-inflammatory cytokines IL-10 and IL-13 were found in treatment groups (columns III and IV, rows 3 and 4) while expression was considerably less in control samples. Magnification is 400× (scale bar, 50 μm). (B) Quantified data revealed an approximate halving of pro-inflammatory cytokine expression when comparing control and treatment groups while anti-inflammatory cytokine expression was higher in treatment groups during this phase of tissue remodeling. *$P < 0.001$, $P < 0.01$, *$P < 0.05$. n.s.=non-significant.

FIG. 6A-F shows chemical structures of anti-inflammatory peptide amphiphiles. The AIF-PAs comprise an anti-inflammatory peptide epitope attached to a contain C16-V3A3E3 PA domain. Upon chemical stimulus, the AIF-PAs undergo self-assembly creating a hydrophobic core and a hydrophilic exterior studded with the anti-inflammatory amino acid epitopes aligning as nanofibers (ref.8; herein incorporated by reference in its entirety).

FIG. 15 shows collagen and vasculature were quantified in regenerated tissue for the additional treatment groups SIS/AIF-PA3, SIS/AIF-PA4 and SIS/AIF-PA5. At 10 days post-augmentation, grafts from treatment groups SIS/AIF-PA3 and SIS/AIF-PA4 demonstrated lower mean collagen levels and greater numbers of vessels/mm2 than control groups. Values for SIS/AIF-PA5 were not significantly different from those of control groups. Treatment effect on vasculature was reduced for SIS/AIF-PA3, SIS/AIF-PA4 and SIS/AIF-PA5, as compared to SIS/AIF-PA1 and SIS/AIF-PA2. Data shown as means±SE. Significance shown for comparison of treatment groups SIS/AIF-PA3, SIS/AIF-PA4 and SIS/AIF-PA5 to control groups SIS (left) and SIS/AIFC-PA6 (right); **$p<0.01$, *$p<0.05$, n.s.=non-significant.

FIG. 16 shows the levels of CD68 and MPO post-augmentation. At 10 days post-augmentation, levels of CD68 and MPO expression were significantly lower in treatment groups SIS/AIF-PA3, SIS/AIF-PA4 and SIS/AIF-PA5 than in control groups. SIS/AIF-PA5 treatment produced the least substantial effect on inflammatory marker expression, a finding consistent with the lowered observed effect on other measures. Data shown as means±SE. Significance shown for comparison of treatment groups SIS/AIF-PA3, SIS/AIF-PA4 and SIS/AIF-PA5 to control groups SIS (left) and SIS/AIFC-PA6 (right); **$P \leq 0.0001$, *$P<0.001$, **$P<0.01$, *$P<0.05$.

DEFINITIONS

Figure 1A:
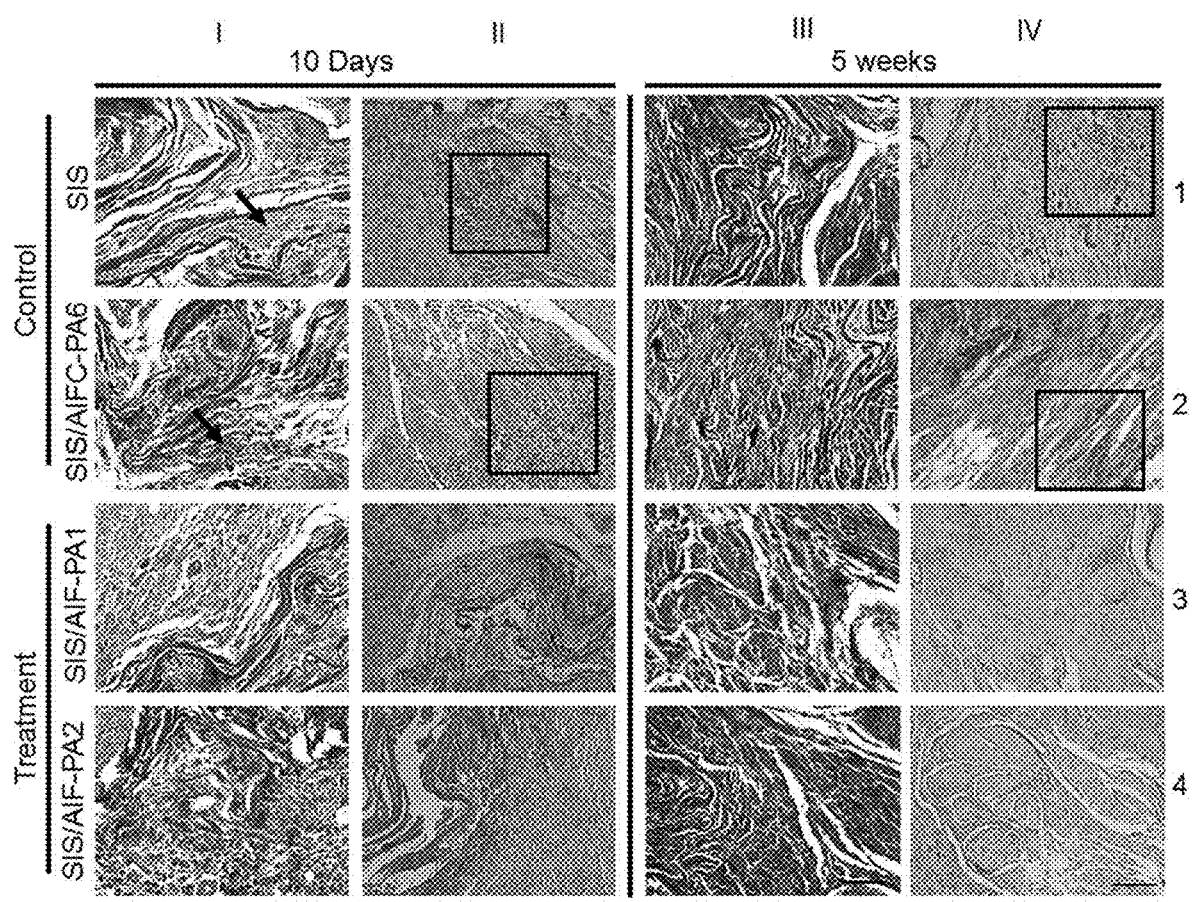
FIG. 1A-C shows histological and morphometric analyses of augmented bladder tissue. (A) Treatment groups demonstrated near-normal physiological collagen content while control group specimens exhibited higher levels of collagen which remained elevated through 5 W. Organized muscle fascicle formation was most notable in treatment groups while still disorganized in control groups at 5 W. Magnification is 400× (scale bar, 50 μm) and 200× (scale bar, 100 μm) for Trichrome and H&E stained samples, respectively. (B) Collagen quantification revealed statistically lower levels of collagen deposition in regenerating bladder in treatment vs. control groups over both time-points. (C) An approximate 2× increase in blood vessel numbers of treatment groups vs. control groups at 10D was observed with an approximate 1.5× increase in the treatment groups at 5 W. Data shown as means±SE. Significance shown for comparison of SIS/AIF-PA1 and SIS/AIF-PA2 to SIS (top) and SIS/AIFC-PA6 (bottom); **$P \leq 0.0001$, *$P < 0.001$, **$P < 0.01$, *$P < 0.05$, n.s.=non-significant.

Although any methods and materials similar or equivalent to those described herein can be used in the practice or testing of embodiments described herein, some preferred methods, compositions, devices, and materials are described herein. However, before the present materials and methods are described, it is to be understood that this invention is not limited to the particular molecules, compositions, methodologies or protocols herein described, as these may vary in accordance with routine experimentation and optimization. It is also to be understood that the terminology used in the description is for the purpose of describing the particular versions or embodiments only, and is not intended to limit the scope of the embodiments described herein.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the embodiments described herein, the following definitions apply.

As used herein and in the appended claims, the singular forms "a", "an" and "the" include plural reference unless the context clearly dictates otherwise. Thus, for example, reference to "a peptide amphiphile" is a reference to one or more peptide amphiphiles and equivalents thereof known to those skilled in the art, and so forth.

The term "amino acid" refers to natural amino acids, unnatural amino acids, and amino acid analogs, all in their D and L stereoisomers, unless otherwise indicated, if their structures allow such stereoisomeric forms.

Natural amino acids include alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (His or H), isoleucine (Ile or I), leucine (Leu or L), Lysine (Lys or K), methionine (Met or M), phenylalanine (Phe or F), proline (Pro or P), serine (Ser or S), threonine (Thr or T), tryptophan (Trp or W), tyrosine (Tyr or Y) and valine (Val or V).

Unnatural amino acids include, but are not limited to, azetidinecarboxylic acid, 2-aminoadipic acid, 3-aminoadipic acid, beta-alanine, naphthylalanine ("naph"), aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, tertiary-butylglycine ("tBuG"), 2,4-diaminoisobutyric acid, desmosine, 2,2'-diaminopimelic acid, 2,3-diaminopropionic acid, N-ethylglycine, N-ethylasparagine, homoproline ("hPro" or "homoP"), hydroxylysine, allo-hydroxylysine, 3-hydroxyproline ("3Hyp"), 4-hydroxyproline ("4Hyp"), isodesmosine, allo-isoleucine, N-methylalanine ("MeAla" or "Nime"), N-alkylglycine ("NAG") including N-methylglycine, N-methylisoleucine, N-alkylpentylglycine ("NAPG") including N-methylpentylglycine. N-methylvaline, naphthylalanine, norvaline ("Norval"), norleucine ("Norleu"), octylglycine ("OctG"), ornithine ("Orn"), pentylglycine ("pG" or "PGly"), pipecolic acid, thioproline ("ThioP" or "tPro"), homoLysine ("hLys"), and homoArginine ("hArg").

The term "amino acid analog" refers to a natural or unnatural amino acid where one or more of the C-terminal carboxy group, the N-terminal amino group and side-chain bioactive group has been chemically blocked, reversibly or irreversibly, or otherwise modified to another bioactive group. For example, aspartic acid-(beta-methyl ester) is an amino acid analog of aspartic acid; N-ethylglycine is an amino acid analog of glycine; or alanine carboxamide is an amino acid analog of alanine. Other amino acid analogs include methionine sulfoxide, methionine sulfone, S-(carboxymethyl)-cysteine, S-(carboxymethyl)-cysteine sulfoxide and S-(carboxymethyl)-cysteine sulfone.

As used herein, the term "peptide" refers an oligomer to short polymer of amino acids linked together by peptide bonds. In contrast to other amino acid polymers (e.g., proteins, polypeptides, etc.), peptides are of about 50 amino acids or less in length. A peptide may comprise natural amino acids, non-natural amino acids, amino acid analogs, and/or modified amino acids. A peptide may be a subsequence of naturally occurring protein or a non-natural (artificial) sequence.

As used herein, the term "artificial" refers to compositions and systems that are designed or prepared by man, and are not naturally occurring. For example, an artificial peptide, peptoid, or nucleic acid is one comprising a non-natural sequence (e.g., a peptide without 100% identity with a naturally-occurring protein or a fragment thereof).

As used herein, the term "peptoid" refers to a class of peptidomimetics where the side chains are functionalized on the nitrogen atom of the peptide backbone rather than to the α-carbon.

As used herein, the term "nanofiber" refers to an elongated or threadlike filament (e.g., having a significantly greater length dimension that width or diameter) with a diameter typically less than 100 nanometers.

As used herein, the term "supramolecular" (e.g., "supramolecular complex," "supramolecular interactions," "supramolecular fiber," "supramolecular polymer," etc.) refers to the non-covalent interactions between molecules (e.g., polymers, marcomolecules, etc.) and the multicomponent assemblies, complexes, systems, and/or fibers that form as a result.

As used herein, the term "physiological conditions" refers to the range of conditions of temperature, pH and tonicity (or osmolality) normally encountered within tissues in the body of a living human.

As used herein, the terms "self-assemble" and "self-assembly" refer to formation of a discrete, non-random, aggregate structure from component parts; said assembly occurring spontaneously through random movements of the components (e.g. molecules) due only to the inherent chemical or structural properties and attractive forces of those components.

As used herein, the term "peptide amphiphile" refers to a molecule that, at a minimum, includes a non-peptide lipophilic (hydrophobic) segment, a structural peptide segment and optionally a functional peptide segment. The peptide amphiphile may express a net charge at physiological pH, either a net positive or negative net charge, or may be zwitterionic (i.e., carrying both positive and negative charges). Certain peptide amphiphiles consist of or comprise: (1) a hydrophobic, non-peptidic segment (e.g., comprising an acyl group of six or more carbons), (2) a β-sheet-forming peptide segment; (3) a carboxyl-rich peptide segment, and (4) a functional moiety.

As used herein and in the appended claims, the term "lipophilic moiety" or "hydrophobic moiety" refers to the moiety disposed on the N-terminus of the peptide amphiphile (e.g., an acyl moiety), and may be herein and elsewhere referred to as the lipophilic or hydrophobic segment or component. The hydrophobic component should be of a sufficient length to provide amphiphilic behavior and micelle (or nanosphere or nanofiber) formation in water or another polar solvent system.

Accordingly, in the context of the embodiments described herein, the hydrophobic component preferably comprises a single, linear acyl chain of the formula: $C_{n-1}H_{2n-1}C(O)$— where n=6-22. In some embodiments, a linear acyl chain is the lipophilic group, palmitic acid. However, other small lipophilic groups may be used in place of the acyl chain.

As used herein, the term "structural peptide" refers to a portion of a peptide amphiphile, typically disposed between the hydrophobic segment and the charged peptide segment. The structural peptide is generally composed of three to ten amino acid residues with non-polar, uncharged side chains (e.g., His (H), Val (V), Ile (I), Leu (L), Ala (A), Phe (F)) selected for their propensity to form hydrogen bonds or other stabilizing interactions (e.g., hydrophobic interactions, van der Waals' interactions, etc.) with structural segments of adjacent structural segments. In some embodiments, nanofibers of peptide amphiphiles having structural peptide segments display linear or 2D structure when examined by microscopy and/or α-helix and/or β-sheet character when examined by circular dichroism (CD).

As used herein, the term "beta (β)-sheet-forming peptide segment" refers to a structural peptide segment that has a propensity to display β-sheet-like character (e.g., when analyzed by CD). In some embodiments, amino acids in a beta (β)-sheet-forming peptide segment are selected for their propensity to form a beta-sheet secondary structure. Examples of suitable amino acid residues selected from the twenty naturally occurring amino acids include Met (M), Val (V), Ile (I), Cys (C), Tyr (Y), Phe (F), Gln (Q), Leu (L), Thr (T), Ala (A), and Gly (G) (listed in order of their propensity to form beta sheets). However, non-naturally occurring amino acids of similar beta-sheet forming propensity may also be used. Peptide segments capable of interacting to form beta sheets and/or with a propensity to form beta sheets are understood (See, e.g., Mayo et al. Protein Science (1996), 5:1301-1315; herein incorporated by reference in its entirety).

As used herein, the term "charged peptide segment" refers to a portion of a peptide amphiphile that is rich (e.g., >50%, >75%, etc.) in charged amino acid residues, or amino acid residue that have a net positive or negative charge under physiologic conditions. A charged peptide segment may be acidic (e.g., negatively charged), basic (e.g., positively charged), or zwitterionic (e.g., having both acidic and basic residues).

As used herein, the terms "carboxy-rich peptide segment," "acidic peptide segment," and "negatively-charged peptide segment" refer to a peptide sequence of a peptide amphiphile that comprises one or more amino acid residues that have side chains displaying carboxylic acid side chains (e.g., Glu (E), Asp (D), or non-natural amino acids). A carboxy-rich peptide segment may optionally contain one or more additional (e.g., non-acidic) amino acid residues. Non-natural amino acid residues, or peptidomimetics with acidic side chains could be used, as will be evident to one ordinarily skilled in the art. There may be from about 2 to about 7 amino acids, and or about 3 or 4 amino acids in this segment.

As used herein, the terms "amino-rich peptide segment", "basic peptide segment," and "positively-charged peptide segment" refer to a peptide sequence of a peptide amphiphile that comprises one or more amino acid residues that have side chains displaying positively-charged acid side chains (e.g., Arg (R), Lys (K), His (H), or non-natural amino acids, or peptidomimetics). A basic peptide segment may optionally contain one or more additional (e.g., non-basic) amino acid residues. Non-natural amino acid residues with basic side chains could be used, as will be evident to one ordinarily skilled in the art. There may be from about 2 to about 7 amino acids, and or about 3 or 4 amino acids in this segment.

As used herein, the term "functional peptide" refers to amino acid sequences that mediate the action of sequences, molecules, or supramolecular complexes associated therewith (e.g., an anti-inflammatory peptide). Peptide amphiphiles and structures (e.g., nanofibers) bearing functional peptides (e.g., anti-inflammatory peptides, etc.) exhibits the functionality of the functional peptide.

As used herein, the term "percent sequence identity" refers to the degree (e.g., 50%, 60%, 70%, 80%, 90%, 95%, 98%, 99%, 100%, ranges therebetween, etc.) to which two polymer sequences (e.g., peptide, polypeptide, nucleic acid, etc.) have the same sequential composition of monomer subunits. If two polymers have identical sequences (e.g., 100% sequence identity) they may be referred to herein as having "sequence identity." The term "percent sequence similarity" refers to the degree (e.g., 50%, 60%, 70%, 80%, 90%, 95%, 98%, 99%, 100%, ranges therebetween, etc.) with which two polymer sequences (e.g., peptide, polypeptide, nucleic acid, etc.) have similar polymer sequences (e.g., only conservative substitutions between the sequences). For example, similar amino acids are those that share the same biophysical characteristics and can be grouped into the families (see "conservative amino acid substitution" below). If two polymers have sequences that have monomers at each position that share the same biophysical characteristics they may be referred to herein as having "sequence similarity." The "percent sequence identity" (or "percent sequence similarity") is calculated by: (1) comparing two optimally aligned sequences over a window of comparison (e.g., the length of the longer sequence, the length of the shorter sequence, a specified window, etc.), (2) determining the number of positions containing identical (or similar) monomers (e.g., same amino acids occurs in both sequences, similar amino acid occurs in both sequences) to yield the number of matched positions, (3) dividing the number of matched positions by the total number of positions in the comparison window (e.g., the length of the longer sequence, the length of the shorter sequence, a specified window), and (4) multiplying the result by 100 to yield the percent sequence identity or percent sequence similarity. For example, if peptides A and B are both 20 amino acids in length and have identical amino acids at all but 1 position, then peptide A and peptide B have 95% sequence identity. If the amino acids at the non-identical position shared the same biophysical characteristics (e.g., both were acidic), then peptide A and peptide B would have 100% sequence similarity. As another example, if peptide C is 20 amino acids in length and peptide D is 15 amino acids in length, and 14 out of 15 amino acids in peptide D are identical to those of a portion of peptide C, then peptides C and D have 70% sequence identity, but peptide D has 93.3% sequence identity to an optimal comparison window of peptide C. For the purpose of calculating "percent sequence identity" (or "percent sequence similarity") herein, any gaps in aligned sequences are treated as mismatches at that position.

A "conservative" amino acid substitution refers to the substitution of an amino acid in a polypeptide with another amino acid having similar properties, such as size or charge. In certain embodiments, a polypeptide comprising a conservative amino acid substitution maintains at least one activity of the unsubstituted polypeptide. A conservative amino acid substitution may encompass non-naturally occurring amino acid residues, which are typically incorporated by chemical peptide synthesis rather than by synthesis in biological systems. These include, but are not limited to, peptidomimetics and other reversed or inverted forms of amino acid moieties. Naturally occurring residues may be divided into classes based on common side chain properties, for example: hydrophobic: norleucine, Met, Ala, Val, Leu, and Ile; neutral hydrophilic: Cys, Ser, Thr, Asn, and Gln; acidic: Asp and Glu; basic: His, Lys, and Arg; residues that influence chain orientation: Gly and Pro; and aromatic: Trp, Tyr, and Phe. Non-conservative substitutions may involve the exchange of a member of one of these classes for a member from another class; whereas conservative substitutions may involve the exchange of a member of one of these classes for another member of that same class.

Any polypeptides described herein as having a particular percent sequence identity or similarity (e.g., at least 70%) with a reference sequence ID number, may also be expressed as having a maximum number of substitutions (or terminal deletions) with respect to that reference sequence. For example, a sequence "having at least Y % sequence identity with SEQ ID NO:Z" may have up to X substitutions relative to SEQ ID NO:Z, and may therefore also be expressed as "having X or fewer substitutions relative to SEQ ID NO:Z."

DETAILED DESCRIPTION

Provided herein are anti-inflammatory nanofibers and methods of use thereof. In particular methods are provided for the use of anti-inflammatory peptide amphiphile (PA) nanofibers in the promotion of tissue (e.g., urinary bladder tissue) regeneration.

Self-assembling peptide amphiphiles (PAs) have demonstrated utility in a wide range of settings and applications (refs.8-10; herein incorporated by reference in their entireties). PAs are comprised of a hydrophobic alkyl segment attached to a peptide domain that includes a β-sheet forming segment. In aqueous environments, these molecules self-assemble through hydrophobic collapse of the alkyl domain in combination with hydrogen bonding in the β-sheet domain to produce high aspect-ratio nanofibers. PAs comprising a bioactive peptide, upon self-assembly into a nanofiber, present the bioactive peptide on the nanofiber surface for recognition by cell receptors or for binding to other biomolecules in order to enhance biological function in vivo (8-10; herein incorporated by reference in their entireties). Specific epitopes useful in the context of tissue regeneration include, but are not limited to, anti-inflammatory sequences (11, herein incorporated by reference in its entirety). In some embodiments, PAs presenting anti-inflammatory epitopes at high density allow for modulation of inflammation-based reactions in a wide array of clinical settings. Experiments conducted during development of embodiments herein demonstrate that application of PAs expressing anti-inflammatory peptides: (1) establishes a comprehensive tissue regenerative milieu, and (2) modulates components of the innate inflammatory response while utilizing a highly pro-inflammatory biological scaffold known to promote tissue fibrosis in a urinary bladder augmentation model (refs.12, 13; herein incorporated by reference in their entireties).

Figure 13:
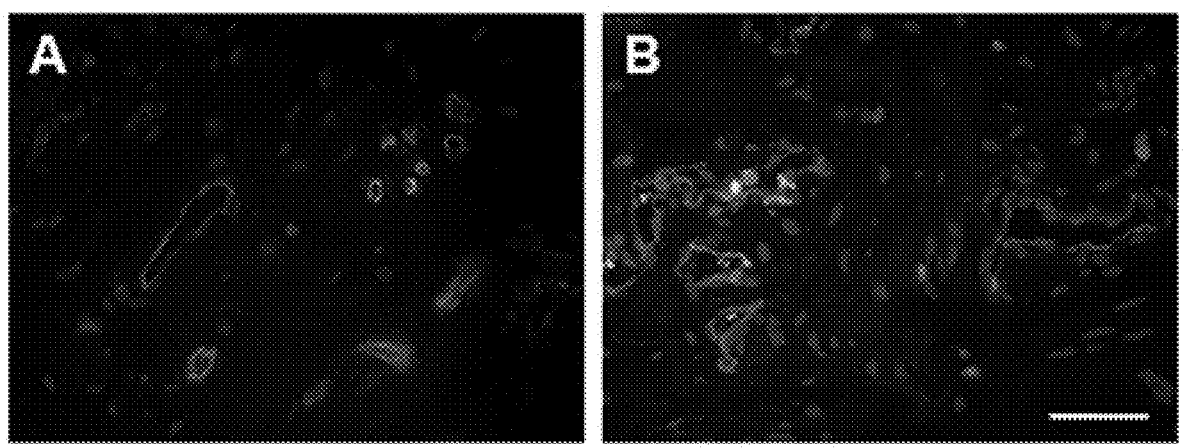
FIG. 13 shows regenerated bladder stained with lectin. In order to determine whether blood vessels in regenerating tissue underwent functional angiogenesis, a fluorochrome conjugated tomato lectin was injected into the animals immediately prior to euthanization to label potential angiogenic vessels. Data clearly demonstrate that newly formed blood vessels in areas of bladder tissue regeneration were patent and functional 5 W post-augmentation. There is also a wide distribution of vessel size suggesting a potential role on vessel development being dictated by the AIF-PAs. Magnification 400× (Scale bar, 50 μm).

Dysregulation of the inflammatory response due to disease, repeated tissue insult, or the use of inflammation-provoking foreign materials for tissue engineering purposes, can lead to excess extracellular matrix tissue deposition (refs.30,31; herein incorporated by reference in their entireties). As this acute inflammatory response can initiate fibrogenesis, in some embodiments, the tempering of this response during initial phases of tissue remodeling is desired (ref.32; incorporated by reference in its entirety). Experiments conducted during development of embodiments herein demonstrated that the application of synthetic PAs expressing potent anti-inflammatory epitopes modulated multiple aspects of tissue regeneration. AIF-PA1 and AIF-PA2 positively altered the regenerative landscape compared to the control AIFC-PA6 or the untreated, highly pro-inflammatory SIS biological scaffold (ref.12,13; herein incorporated by reference in their entireties). Specifically, collagen distribution in regenerating tissue was significantly reduced while there was a striking increase in tissue blood vessel regeneration that comprised functional, patent blood vessels (FIG. 13). Normal tri-layer bladder architecture was also observed in treatment groups as control groups demonstrated disorganized tissue organization even at 5 weeks post-surgery (FIG. 1A, column III). This was coupled with a striking reduction in the levels of inflammatory cells found in the grafted areas typically seen at the onset of an innate immune response to injury. Physiological bladder function was superior in AIF-PA1 animals compared to controls. This demonstrates the feasibility of utilizing anti-inflammatory agents in a highly invasively surgical setting in the presence of a foreign body which allows for functional tissue regeneration.

Acute inflammation due to repetitive insult or inflammatory dysregulation is the precursor to chronic inflammatory events with the resulting byproduct ending in permanent scarring or fibrosis (ref.33; herein incorporated by reference in its entirety). This process is in part caused by the accumulation of extracellular matrix products in and around regenerating tissue creating an inhospitable growth environment. In typical bladder augmentation models that utilize biologic or synthetic scaffolding material as a three-dimensional architectural foundation, the accumulation of excess collagen is a major obstacle that is typically encountered. It has been demonstrated that unseeded scaffolds contain approximately 78% collagen at 5 weeks post-augmentation with no resolution of these events as the collagen level increased to approximately 86% at the 10 week time-point of this study in a small animal model (ref.17; herein incorporated by reference in its entirety). In a similar bladder augmentation setting, non-physiological collagen levels were also observed in a non-human primate model of bladder regeneration leading to tissue fibrosis (ref.13; herein incorporated by reference in its entirety). The typical ratio of muscle to collagen in the bladder is approximately 1:1 across a variety of species (refs.15,34,35; herein incorporated by reference in their entireties). Drastic deviation from this ratio leads to bladder dysfunction.

Figure 8:
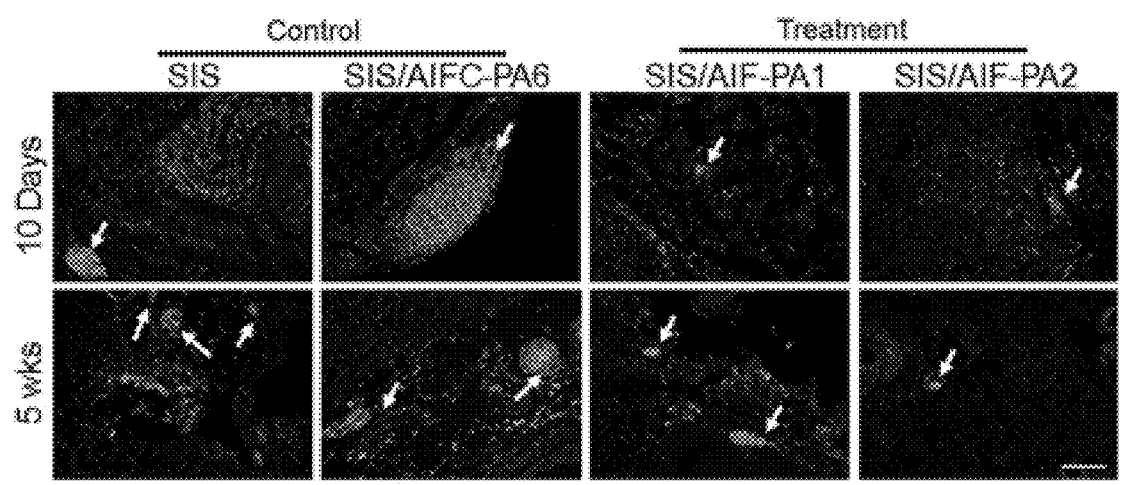
FIG. 8 shows granulation tissue formation in the bladders of SIS and SIS/AIF-PA augmented animals. Granulation tissue is composed of several extracellular matrices such as collagen and a variety of immune cell types including lymphocytes, neutrophils, and especially macrophages (refs.54-56; herein incorporated by reference in their entireties). Extravesical granulomas were found in regenerating bladder muscle and submucosa but not in the epithelial layer (urothelium) that lines the interior of the bladder wall. No necrosis was observed at the core or at the periphery of the granulation tissue at either time-point. Granulation tissue was identified by a trained Pathologist (M.D.H.) utilizing immunofluorescence imaging with the macrophage marker CD68 (green). 10 day treatment samples (row 1) demonstrated large granuloma formation (concentrated areas of macrophage infiltration) areas in SIS and AIFC-PA6 groups throughout the augmented area that were high in frequency. AIF-PA1 and AIF-PA2 groups demonstrated a lesser degree of granuloma formation in size and frequency. 5 W treatment samples (row 2) further demonstrated the accumulation of granulomas in SIS and AIFC-PA6 groups while these levels were diminished in AIF-PA1 and AIF-PA2 groups. Images are representative examples of multiple stained tissue samples. See Table 1 for granuloma quantification. Magnification 100× (Scale bar, 200 μm).

Secondary examples of fibrosis include the implantation of artificial organs and medical devices (ref.36; herein incorporated by reference in its entirety). Soft tissue metal implants, including titanium based structures, possess a proclivity to commence inflammatory reactions resulting in tissue fibrosis (ref.37; herein incorporated by reference in its entirety). It is contemplated that the innate immune response, particularly the M1 macrophage component, is responsible for eventual fibrosis. Therefore, in some embodiments, coating implantable devices with the AIF-PAs described herein is beneficial in clinical applications by lessening localized macrophage accumulation and subsequently fibrosis; although the embodiments herein are not limited to any particular mechanism of action and an understanding of the mechanism of action is not necessary to practice such embodiments. Experiments conducted during development of embodiments herein further indicate that the treatment group AIF-PAs had a profound effect on the granuloma formation (a precursor to fibrosis). The frequency and size of granulomas was markedly disparate between groups (FIG. 8, Table 1). There were approximately 10.5 granulomas observed in bladder tissue of control samples as opposed to approximately 4 in treatment groups. The numbers of granulomas subsided over time but there were still significant levels found at the 5 week time-point in the control groups. Granuloma levels found in treatment groups were drastically reduced although tissue necrosis and the core of granulomas were not observed in any setting. This data is compelling due to the diminutive size of the rodent bladder and its relationship to the granuloma size and frequency within the bladder.

Figure 6A:
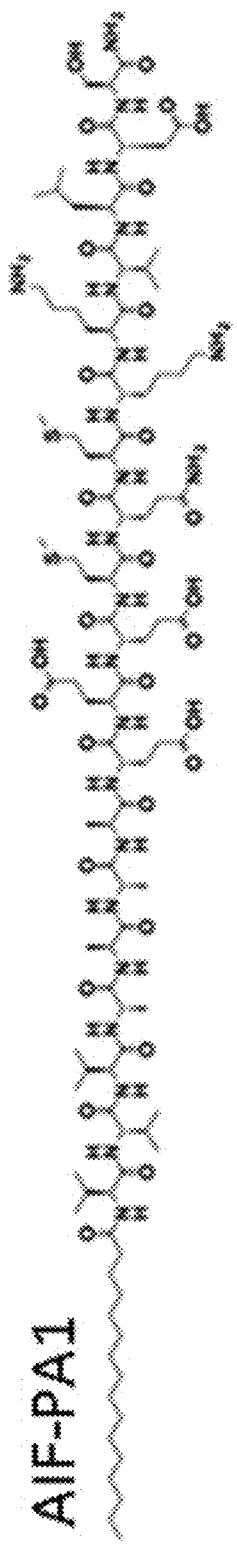
Figure 6B:
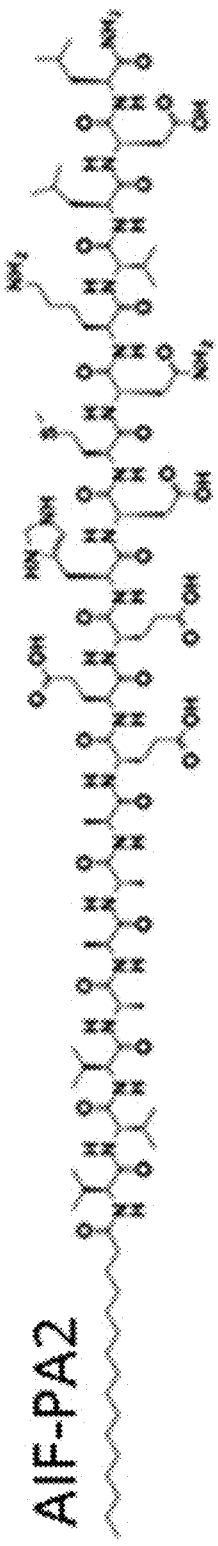
Figure 6C:
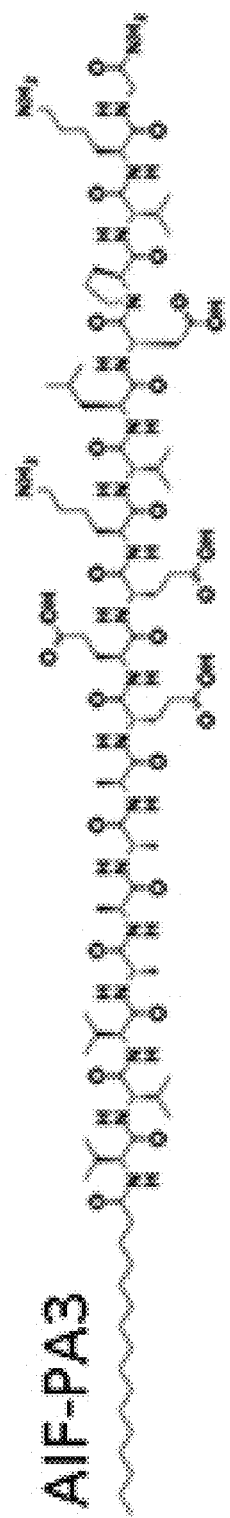
Figure 6D:
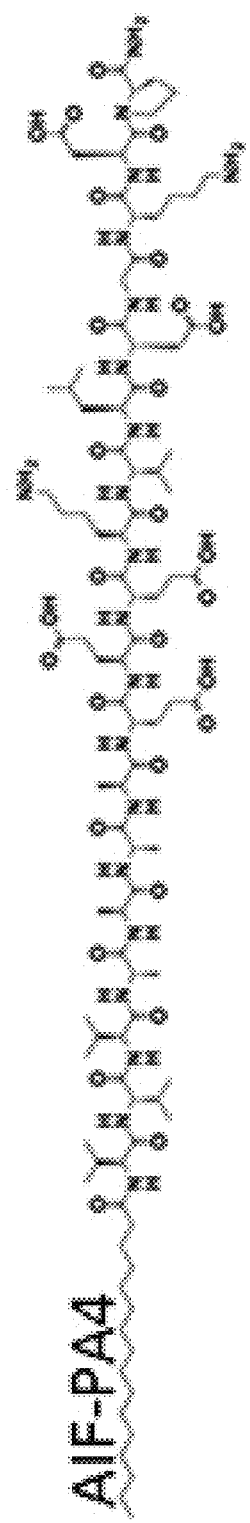
Figure 6G:
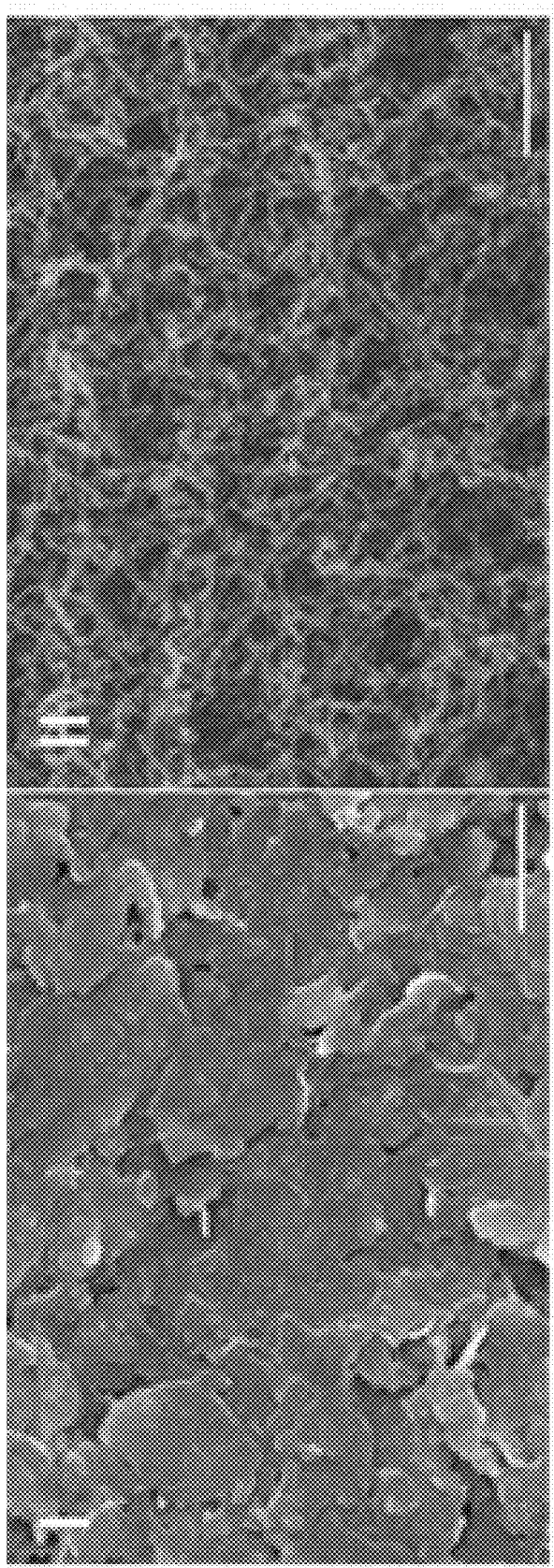
FIG. 6G shows small intestinal submucosa (SIS), a decellularized biological scaffold obtained from porcine intestines, was utilized specifically for bladder augmentation surgery due to its inflammation evoking nature (refs.12,13, 16; herein incorporated by reference in their entireties). Image I depicts an uncoated piece of SIS scaffold that has undergone scanning electron microscopy. The surface is speckled with asymmetric remnants of biological matter. Analogously, a similar piece of SIS that has been dip-coated with an AIF-PA displays prominent nanofiber structures throughout the scaffold, seen in image II. The self-assembled nanofibers create a vast network on what would eventually become the luminal and extra-luminal side of the bladder. The epitope expression on the nanofibers has previously been computed to be at high levels (ref.10; herein incorporated by reference in its entirety). (Scale bar, 1 μm.).

Modulation of cytokine expression in an inflammatory environment is important for proper wound healing and functional tissue regeneration. Exacerbation of tissue injury is typically due to the abundance of pro-inflammatory cytokines in regenerating tissue. IL-1β and TNFα secreted by M1 macrophages are key perpetrators and initiators of fibrogenesis (refs.38,39; herein incorporated by reference in its entirety). The blockage of TNFα expression to prevent tissue damage and resulting fibrosis has been the focus of multiple clinical studies (refs.40,41; herein incorporated by reference in their entireties). Bongartz et al. describe the systemic delivery of chimeric monoclonal antibodies against TNFα for patients with rheumatoid arthritis which was accompanied by serious side effects. In a similar fashion, IL-1β has also been the target of antibody therapy (ref.42; herein incorporated by reference in its entirety). However, the systemic delivery of the aforementioned agents has caused serious side effects including the increased risk malignant transformation (ref.40; herein incorporated by reference in its entirety). Experiments were conducted during development of embodiments herein that demonstrate the statistically significant reduction in expression of IL-1δ and TNFα in treatment groups when compared to controls accompanied by the increase in the levels of the anti-inflammatory cytokines IL-10 and IL-13 (See, e.g., FIG. 4B). The approximate halving of IL-1β and TNFα levels at 10 days is quite cogent. Experiments indicate that the dramatic decrease in pro-inflammatory cytokine expression is the result of two key features of this system. The first being the localized delivery of the AIF-PAs as the SIS was thoroughly coated immediately prior to surgery. Second is the high density of peptide epitopes expressed on the AIF-PAs (FIG. 6G). However, the embodiments herein are not limited to any particular mechanism of action and an understanding of the mechanism of action is not necessary to practice the such embodiments. Epitope expression on the nanofiber surface of PAs can be as high as $1 \times 10^{14}$ epitopes/$cm^2$ (ref.10; herein incorporated by reference in its entirety). This allows for concentrated delivery of the AIF-PAs in a given tissue area that could outperform any type of liquid or most other solid state delivery vehicles.

Figure 14:
FIG. 14 shows the evaluation of bladder stones formed in regenerating bladders. Bladder stone formation can be caused by a myriad of factors including those based upon diet as well as genetic makeup and underlying bladder conditions (refs.57,58; herein incorporated by reference in its entirety). Animals in the control groups (SIS alone, SIS/AIFC-PA6) demonstrated an apparent propensity to form stones that were quite large in size as compared to the overall volume of the bladder treatment group samples (SIS/AIF-PA1 and SIS/AIF-PA2) formed stones that were a fraction of the size found in control animals. The frequency of stone formation is presented in Table 3.

The ability to recreate physiologically relevant organ function following substantial insult is a major goal of regenerative medicine based strategies. UDS testing provided physiological bladder data in the form of bladder pressures and voiding patterns of regenerating bladder tissue. Proximate measurements including bladder capacity determinations pre- and post-surgery help contribute to the understanding of the intricate relationship between architectural bladder tissue regeneration and physiological function. In typical pathologic bladders, high intravesical pressures due to uninhibited contractions or high voiding pressures are associated with kidney damage due to reverse transduction of the pressure (ref.43; herein incorporated by reference in its entirety). SIS/AIF-PA1 and SIS/AIF-PA2 demonstrated a decreased slope of the filling curve indicating an increase in compliance of the bladder as filling volume changes which led to a slower rise in intravesical pressures. A decrease of intravesical pressures was also observed during voiding thus fulfilling the demands of a successful augmentation. In contrast, augmentation with SIS alone and SIS/AIFC-PA6 failed to decrease intravesical pressures. It is contemplated that coating SIS with AIF-PA1 or AIF-PA2 is associated with an improved incorporation of the SIS into the bladder environment that promotes timely development of newly formed native tissue along the SIS. The AIF-PAs were also able to limit bladder stone formation possibly through modulation of inflammatory cytokine expression (FIG. 14, Table 5) (ref.44; herein incorporated by reference in its entirety). Physiological testing data indicate that AIF-PA coated SIS can successfully be employed for bladder augmentations leading to an improved pressure profile during filling and voiding.

Constituents of the inflammatory response to tissue injury involve both innate (including the complement system) and adaptive arms of the immune system that can either contribute to the resolution of volatile or dysfunctional tissue inflammatory responses or exacerbate the process leading to the formation of scar tissue (refs.45,46; herein incorporated by reference in their entireties). The latter process is seen in a number of organ systems including those urological in nature and those relevant to cardiac repair post-myocardial infarction (refs.47,48; herein incorporated by reference in their entireties). In this setting, regulatory T-lymphocytes have been demonstrated to attenuate the inflammatory response following a major myocardial infarct in order to prevent unfavorable tissue remodeling events through pro-inflammatory cytokine inhibition of cardiomyocytes (ref.49;

herein incorporated by reference in its entirety). There is considerable functional overlap with regard to the role of T-lymphocytes in the inflammatory response (refs.50-53; herein incorporated by reference in their entireties). However, in order to solely study the early innate immune response with regard to inflammation, the T-lymphocyte deficient animal model was selected in order to gain better insight into the precise role this arm of the immune system may play without interference of the T-lymphocyte response.

Experiments conducted during development of embodiments herein have demonstrated that the application of AIF-PAs in a bladder regenerative setting possess the ability to assuage the innate immune response and promotes anatomically correct and physiologically functional bladder tissue. The supplementation of SIS biological scaffolds with AIF-PA1 and AIF-PA2 greatly reduced collagen content while simultaneously providing substantial growth advantages to the regenerating bladder including increased tissue vascularization and muscle growth in areas of regeneration. This was accompanied by superior bladder functional recovery as demonstrated by urodynamic studies. Treatment AIF-PAs decreased levels of pro-inflammatory macrophages while positively modulating cytokine expression along with decreasing granuloma- and bladder stone formation.

In some embodiments, the peptide amphiphile molecules and compositions of the embodiments described herein are synthesized using preparatory techniques well-known to those skilled in the art, preferably, by standard solid-phase peptide synthesis, with the addition of a fatty acid in place of a standard amino acid at the N-terminus of the peptide, in order to create the lipophilic segment. For example, synthesis typically starts from the C-terminus, to which amino acids are sequentially added using either a Rink amide resin (resulting in an —NH2 group at the C-terminus of the peptide after cleavage from the resin), or a Wang resin (resulting in an —OH group at the C-terminus). Accordingly, embodiments described herein encompasses peptide amphiphiles having a C-terminal moiety that may be selected from the group consisting of —H, —OH, —COOH, —CONH$_2$, and —NH$_2$. The lipophilic or hydrophobic segment is typically incorporated at the N-terminus of the peptide after the last amino acid coupling, and is composed of a fatty acid or other acid that is linked to the N-terminal amino acid through an acyl bond. In aqueous solutions, PA molecules self-assemble (e.g., into cylindrical micelles (a.k.a nanofibers)) that bury the lipophilic segment in their core and display the functional peptide on the surface. The structural peptide undergoes intermolecular hydrogen bonding to form beta sheets that orient parallel to the long axis of the micelle. The functional peptide (e.g., anti-inflammatory peptide is presented on the surface of the nanofiber.

In some embodiments, compositions described herein comprise PA building blocks that in turn comprise a hydrophobic segment and a peptide segment. In certain embodiments, a hydrophobic (e.g., hydrocarbon and/or alkyl tail) segment of sufficient length (e.g., >3 carbons, >5 carbons, >7 carbons, >9 carbons, >11, >13, >15, etc.) is covalently coupled to peptide segment (e.g., an ionic peptide having a preference for beta-strand conformations) to yield a peptide amphiphile molecule. In some embodiments, a plurality of such PAs will self-assemble in water (or aqueous solution) into a nanostructure (e.g., nanofiber). In various embodiments, the relative lengths of the peptide segment and hydrophobic segment result in differing PA molecular shape and nanostructural architecture. For example, a broader peptide segment and narrower hydrophobic segment results in a generally conical molecular shape that has an effect on the assembly of PAs (See, e.g., J. N. Israelachvili Intermolecular and surface forces; 2nd ed.; Academic: London San Diego, 1992; herein incorporated by reference in its entirety). Other molecular shapes have similar effects on assembly and nanostructural architecture. In various embodiments, hydrophobic segments pack in the center of the assembly with the peptide segments exposed to an aqueous or hydrophilic environment to form cylindrical nanostructures that resemble filaments. Such nanofilaments display the peptide regions on their exterior and have a hydrophobic core.

In some embodiments, to induce self-assembly of an aqueous solution of peptide amphiphiles, the pH of the solution may be changed (raised or lowered) or multivalent ions, such as calcium, or charged polymers or other macromolecules may be added to the solution.

In some embodiments, the hydrophobic segment is a non-peptide segment (e.g., alkyl group). In some embodiments, the hydrophobic segment comprises an alkyl chain (e.g., saturated) of 4-25 carbons (e.g., 4, 5, 6, 7, 8, 9, 10, 11, 12, 13, 14, 15, 16, 17, 18, 19, 20, 21, 22, 23, 24, 25), fluorinated segments, fluorinated alkyl tails, aromatic segments, pi-conjugated segments, etc. In some embodiments, the hydrophobic segment comprises an acyl chain (e.g., saturated) of 4-25 carbons (e.g., 4, 5, 6, 7, 8, 9, 10, 11, 12, 13, 14, 15, 16, 17, 18, 19, 20, 21, 22, 23, 24, 25)

In some embodiments, peptide amphiphiles comprise a functional moiety. In particular embodiments, a functional moiety is the C-terminal most segment of the PA. In some embodiments, the functional moiety is attached to the C-terminal end of the charged segment. In other embodiments, a functional moiety is the N-terminal most segment of the PA. In some embodiments, the functional moiety is attached to the N-terminal end of the charged segment. In some embodiments, the functional moiety is exposed on the surface of an assembled PA structure (e.g., nanofiber). A functional moiety is typically a peptide (e.g., anti-inflammatory peptide, etc.), but is not limited thereto. Examples described in detail herein utilize a peptide sequence that produces an anti-inflammatory response and/or aids in tissue regeneration. Functional peptides and other moieties for achieving functionality will be understood.

Suitable peptide amphiphiles, PA segments, PA nanostructures, and associated reagents and methods for use in some embodiments herein are described, for example in U.S. Pat. Nos. 8,512,693; 8,450,271; 8,138,140; 8,124,583; 8,114,835; 8,114,834; 8,080,262; 8,063,014; 7,851,445; 7,838,491; 7,745,708; 7,683,025; 7,554,021; 7,544,661; 7,534,761; 7,491,690; 7,452,679; 7,390,526; 7,371,719; 6,890,654; herein incorporated by reference in their entireties.

The characteristics (e.g., shape, rigidity, hydrophilicity, etc.) of a PA supramolecular structure depend upon the identity of the components of a peptide amphiphile (e.g., lipophilic segment, acidic segment, structural segment, functional segment, etc.). For example, nanofibers, nanospheres, intermediate shapes, and other supramolecular structures are achieved by adjusting the identity of the PA component parts.

In particular embodiments, the compositions and methods herein find use in preventing or reducing inflammation; however, applications are not so limited. Compositions and methods herein may find use more broadly in tissue regeneration applications (e.g., bladder tissue regeneration), other medical applications, or other non-medical materials applications.

In some embodiments, PAs comprise functional peptide segments that provide an anti-inflammatory functionality. In some embodiments, anti-inflammatory peptides are exposed on the surface of PA nanofibers. In some embodiments, peptide amphiphiles comprise an anti-inflammatory peptide or peptide sequence with 50% or greater sequence identity (e.g., 50%, 60%, 70%, 80%, 90%, 100%, or ranges therebetween) with one of MQMKKVLDS (SEQ ID NO:7), HDMNKVLDL (SEQ ID NO:8), KVLDPVKG (SEQ ID NO:9), KVLDGQDP (SEQ ID NO:10), or DPVKG (SEQ ID NO:11). In some embodiments, peptide amphiphiles comprise an anti-inflammatory peptide or peptide sequence with 50% or greater sequence similarity (e.g., 50%, 60%, 70%, 80%, 90%, 100%, or ranges therebetween) with one of MQMKKVLDS (SEQ ID NO:7), HDMNKVLDL (SEQ ID NO:8), KVLDPVKG (SEQ ID NO:9), KVLDGQDP (SEQ ID NO:10), or DPVKG (SEQ ID NO:11). In some embodiments, peptide amphiphiles comprise an anti-inflammatory peptide or peptide sequence with 5 or fewer (e.g., 5, 4, 3, 2, 1) non-conservative substitutions relative to MQMKKVLDS (SEQ ID NO:7), HDMNKVLDL (SEQ ID NO:8), KVLDPVKG (SEQ ID NO:9), KVLDGQDP (SEQ ID NO:10), or DPVKG (SEQ ID NO:11). In some embodiments, peptide amphiphiles comprise an anti-inflammatory peptide or peptide sequence with 8 or fewer (e.g., <8, <7, <6, <5, <4, <3, <2, <1) conservative substitutions relative to MQMKKVLDS (SEQ ID NO:7), HDMNKVLDL (SEQ ID NO:8), KVLDPVKG (SEQ ID NO:9), KVLDGQDP (SEQ ID NO:10), or DPVKG (SEQ ID NO:11). In some embodiments, an anti-inflammatory peptide or peptide sequence comprises MQMKKVLDS (SEQ ID NO:7), HDMNKVLDL (SEQ ID NO:8), KVLDPVKG (SEQ ID NO:9), KVLDGQDP (SEQ ID NO:10), or DPVKG (SEQ ID NO:11).

In some embodiments, PAs comprise a structural peptide segment forms interactions (e.g., beta sheet formation) between PAs within a nanofiber. In some embodiments, structural peptides form the surface of PA nanofibers (e.g., with functional peptides extending therefrom). In some embodiments, peptide amphiphiles comprise structural peptide or peptide sequence with 50% or greater sequence identity (e.g., 50%, 60%, 70%, 80%, 90%, 100%, or ranges therebetween) with one of VVVAAAEEE (SEQ ID NO:12), VVVAAA (SEQ ID NO:13), or VVAA (SEQ ID NO:14). In some embodiments, peptide amphiphiles comprise structural peptide or peptide sequence with 50% or greater sequence similarity (e.g., 50%, 60%, 70%, 80%, 90%, 100%, or ranges therebetween) with one of VVVAAAEEE (SEQ ID NO:12), VVVAAA (SEQ ID NO:13), or VVAA (SEQ ID NO:14). In some embodiments, peptide amphiphiles comprise a structural peptide or structural peptide sequence with 5 or fewer (e.g., 5, 4, 3, 2, 1) non-conservative substitutions relative to VVVAAAEEE (SEQ ID NO:12), VVVAAA (SEQ ID NO:13), or VVAA (SEQ ID NO:14). In some embodiments, peptide amphiphiles comprise an anti-inflammatory peptide or peptide sequence with 8 or fewer (e.g., <8, <7, <6, <5, <4, <3, <2, <1) conservative substitutions relative to VVVAAAEEE (SEQ ID NO:12), VVVAAA (SEQ ID NO:13), or VVAA (SEQ ID NO:14). In some embodiments, a structural peptide or structural peptide sequence comprises VVVAAAEEE (SEQ ID NO:12), VVVAAA (SEQ ID NO:13), or VVAA (SEQ ID NO:14).

In some embodiments, PAs and nanofibers described herein find use with additional compositions, materials, and systems for tissue (e.g., bladder tissue regeneration), including but not limited to those described in, for example: U.S. Pat. Pub. 2010/0316614; U.S. Pat. No. 7,579,189; WO 2010/054013; U.S. Pat. No. 5,645,860; WO 2003/007879; herein incorporated by reference in their entireties.

EXPERIMENTAL

Example 1

Materials and Methods

Anti-Inflammatory Peptide Amphiphile Synthesis

Anti-inflammatory peptide amphiphiles (AIF-PAs) were synthesized utilizing standard fluoroen-9-ylmethoxycarbonyl (Fmoc) solid phase peptide synthesis (SPPS) procedures (ref.8; herein incorporated by reference in its entirety). The AIF-PAs were synthesized from the C terminus to N terminus, with Rink Amide MBHA (4-(2',4'-Dimethoxyphenyl-Fmoc-aminmethyl)-phenoxyacetamido-methylbenzhydryl amine resin) at the C terminus as the solid state support for the addition of Fmoc-protected AA. The Fmoc group was removed by agitating the resin in a solution of 30% piperidine in dimethylformamide (DMF) (v/v) for 10 minutes. This step was performed twice at the beginning of each AA coupling step. This was followed by a wash with dichloromethane (DCM), two washes with DMF, and finally two final washes in DCM. A Ninhydrin test was performed to confirm the presence of an N-terminus free amine indicated by a positive color change to purple. The AA coupling cocktail consisted of a 4× molar excess of the Fmoc AA, 3.95× molar excess of β-Benzotriazole-N,N,N',N'-tetramethyl-uronium-hexafluoro-phosphate (HBTU), and a 6× molar excess of N,N-diisopropylethylamine (DIEA) all relative to the resin. The AA, HBTU, and DIEA were dissolved in approximately 20 mL of DMF. Once the Ninhydrin test confirmed the presence of free amino termini, the AA coupling cocktail was added to the resin and agitated for a minimum of 3 hours. Following agitation, the resin was washed thoroughly with DMF 3× for approximately one minute per wash and subsequently washed with DCM twice. A final Ninhydrin test was performed to confirm the AA had been coupled successfully indicated by a no color change. The remaining AA was added as described. Following the addition of the AA sequence, a hydrophobic tail (e.g., palmitic acid (C16) tail) was coupled for 2 hours at 4× molar excess with 3.95× and 6× molar excess of HBTU and DIEA, respectively, dissolved in a 20:80 mixture of DCM:DMF.

To cleave the finished AIF-PA from the resin, a solution containing 95% trifluoroacetic acid (TFA), 2.5% triisopropylsilane (TIS), and 2.5% nanopure water was mixed with the resin and agitated for at least 3 hours. The solution was isolated from the resin into a 500 mL round bottom flask, and the resin was washed once with DCM. The TFA was removed using a rotary evaporator (R-210; Buchi Analytical Inc.) at 50° C. Cold diethyl ether was added to remove soluble protecting groups remaining after cleaving and precipitate the AIF-PAs. The AIF-PA diethyl ether solution was centrifuged and decanted, leaving only the AIF-PA precipitate, which was then dried under vacuum for 2 days. Following cleavage, the AIF-PAs were purified via RP-HPLC (Varian Prostar; Varian Inc.) under either acidic (C-18 Atlantis Column; Waters Corp.) or basic (C-18 Gemini Column; Phenomenx Inc.) conditions based on the net charge of the complete AIF-PA at physiological pH. Purification was monitored by UV/Vis spectroscopy at 220 nm and 325 nm. Fractions of interest were confirmed to contain the target AIF-PA via mass spectrometry (6510 Q-TOF LC/MS 1200 Series; Agilent Technologies). Following purification, the AIF-PAs were subject to rotary evaporation before being lyophilized (FreeZone Plus 6; Labconco Corp.) for 3 days. Dried samples were stored at −20° C. until needed. The AA sequences (with the bioactive epitope in bold) of the AIF-PAs utilized throughout the experiments conducted during development of embodiments herein were: AIF-PA1: $C_{16}$-VVVAAAEEEMQMKKVLDS (SEQ ID NO:1); AIF-PA2: $C_{16}$-VVVAAAEEEHDMNKVLDL (SEQ ID NO:2); AIF-PA3: $C_{16}$-VVVAAAEEEKVLDPVKG (SEQ ID NO:3); AIF-PA4: $C_{16}$-VVVAAAEEEKVLDGQDP (SEQ ID NO:4); AIF-PA5: $C_{16}$-VVVAAAEEEDPVKG (SEQ ID NO:5); AIFC-PA6 (Control): $C_{16}$-VVVAAAEEEKLMSQKMVD (SEQ ID NO:6). AIFC-PA6 expressed a scrambled AA sequence that served as a control throughout experiments. Sequences were derived from studies of the uteroglobin protein (refs.11,14; herein incorporated by reference in their entireties).

Scanning Electron Microscopy of SIS Scaffolds

Scanning electron microscopy (SEM) was performed using a Hitachi 54800-II scanning electron microscope (Hitachi Inc.) with a 5 kV accelerating voltage. To prepare samples for imaging, a sample of SIS coated with an AIF-PA was prepared by identical methods as were used for in vivo studies. An AIF-PA solution, induced to form a gel using a $CaCl_2$) solution, was coated onto one side of the surface of an SIS scaffold. The sample was fixed in 2% glutaraldehyde and 3% sucrose in phosphate buffered saline (PBS) for 30 minutes at 4° C. followed by sequential dehydration in an ascending series of ethanol. The scaffold was then dried at the critical point and coated with 8 nm 0s04 prior to imaging. Images were collected of both the SIS surface alone and a representative sample of SIS with AIF-PA on the surface.

Rat Bladder Augmentation Model

Athymic female rats (weighing ~200 g and 8-10 weeks old; National Cancer Institute Animal Production Program) underwent bladder augmentation (ref.15; herein incorporated by reference in its entirety). Athymic rats were chosen for this study to solely examine the innate immune response to inflammation without influence of the adaptive immune response. In order to induce anesthesia, animals were given intraperitoneal injections of 60 mg/kg ketamine and 5 mg/kg xylazine. A second injection consisting of Buprenex (1 mg/kg) was administered subcutaneously to alleviate any pain/discomfort during and following surgical procedures. An approximate 1.5 cm midline vertical skin incision was created to expose the abdominal fascia and muscles. This was immediately followed by the separation of the wall leading to the identification of the bladder. An approximate 70% supratrigonal cystectomy was performed from anterior to posterior creating a clamshell. Immediately prior to bladder augmentation procedures, samples of the pro-inflammatory biological scaffold, small intestinal submucosa (SIS (0.5×0.5 cm); Cook Biotech.) (refs.12,13,16; herein incorporated by reference in their entireties) were thoroughly dip-coated separately in one of the previously described AIF-PAs following gelation procedures. The sections of SIS were dip-coated for approximately 20 seconds and allowed to adhere to the SIS for an additional 30 seconds. Dip-coating procedures were performed at room temperature in air. The cystectomized bladder defect was then augmented with: 1) SIS (non-AIF-PA coated SIS; n=8 animals over both time-points); 2) AIF-PA1 coated SIS (denoted as SIS/AIF-PA1; n=11 animals over both time-points); 3) AIF-PA2 coated SIS (denoted as SIS/AIF-PA2; n=8 animals over both time-points); 4) AIF-PA3 coated SIS (denoted as SIS/AIF-PA3; n=3); 5) AIF-PA4 coated SIS (denoted as SIS/AIF-PA4; n=3 animals); 6) AIF-PA5 coated SIS (denoted as SIS/AIF-PA5; n=3 animals); and 7) AIFC-PA6 coated SIS (denoted as SIS/AIFC-PA6; n=9 animals over both time-points). The bladder was finally covered with omentum after being closed in a watertight manner utilizing 7-0 polyglactin suture. The abdominal wall was then closed in a single layer with 5-0 ethibond running suture and the skin re-approximated with 9 mm autoclips. Each group was sacrificed at 10 day and 5 week time-points.

Histological Staining and Quantification of Augmented SIS/Tissue Samples

Explanted bladder specimens encompassing the entire thickness of the bladder were isolated immediately following euthanasia and processed (ref.15; herein incorporated by reference in its entirety). Specimens were fixed in a 10% buffered formalin phosphate (Fisher Scientific, Inc.) solution followed by a series of graded ethanol exchanges then embedded in paraffin (Fisher Scientific). Embedded tissues were sectioned onto glass slides at a thickness of 10 μm using a R1\42125 RT Microtome (Leica) onto glass slides and subjected to staining with Masson's Trichrome (Sigma-Aldrich Corp.) reagent. The paraffin was removed from tissue containing slides using a hot plate at 62° C. for 6 minutes and was followed by treatment with xylenes, graded ethanol washes and DI water. Slides were placed in Bouin's solution (Sigma-Aldrich Corp.) for approximately 15 min then rinsed under running tap water. The samples were then stained 5 minutes with Hematoxylin and rinsed with running water and subsequently stained with Scarlet-Acid Fuchsin (Sigma-Aldrich Corp.). Slides were rinsed again with DI water and placed into a mixture of PTA/PMA, followed by Aniline Blue solution and a 1% acetic acid wash. Finally, slides were placed in 95-100% ethanol and rinsed in xylene. Following air drying, a coverslip was placed over the specimen sample and secured with Permaslip (Alban Scientific Inc.).

Bladder Tissue Collagen Quantification

Bladder tissue specimens were evaluated for collagen content (refs.13,15,17; herein incorporated by reference in their entireties). Collagen from Trichrome stained samples was quantified digitally utilizing a Nikon Eclipse 50i Microscope (Nikon Inc.) and Spot Advanced Imaging Software (Diagnostic Instruments). Sample images (1600 pixels× 1200 pixels, bit depth 24) were opened with Adobe Photoshop CS3 (Adobe Systems Inc.). The contrast of red pixels from blue pixels was enhanced by a two-fold elevation of magenta levels followed by a two-fold depression of cyan levels in the red and magenta spectra. This contrast was further improved by a two-fold elevation of cyan levels followed by a two-fold depression of magenta levels in the cyan and blue spectra. The selection color range tool with a fuzziness level of 115% was then used to digitally select the red or blue pixels of the entire image. Selected pixels were subsequently quantified using the image histogram tool and a muscle to collagen ratio was calculated from these values. In cases where urothelial cells, red blood cells, debris, and the SIS scaffold were present, images were edited to remove these structures to preserve a more accurate extrapolation of the collagen content from the red:blue. Areas of regenerated tissue were subjected to an average of ten, random microscopic fields to determine collagen levels at 10 day and 5 week time-points. Data was based upon ten images per animal for each group at 10 day and 5 week time-points.

Blood Vessel Quantification in Areas of Bladder Tissue Regeneration

Trichrome sample images were opened with Adobe Photoshop CS3 and were initially characterized utilizing a Nikon Eclipse 50i Microscope in addition to Spot Advanced Imaging Software. Vessel numbers were quantified utilizing the pen tool based upon n=10 images per graft in regenerated areas. Individual vessels were selected manually and subsequently quantified using the image histogram tool to acquire pixel density for each vessel. Data is represented as mean number of vessels/mm$^2$ (means±SE).

Characterization of Immunofluorescence Stained Augmented Tissues

Tissue sections comprised of SIS alone, SIS/AIF-PA1, SIS/AIF-PA2, and SIS/AIF-PA6 augmentations were subjected to immunofluorescence staining by initially undergoing antigen retrieval which consisted of 15 min of boiling in citrate buffer (0.01M citrate solution, pH 6.0 with 0.05% Tween-20) followed by cooling at room temperature for approximately 20 minutes. The antibody staining process consisted of a blocking step for 15 min in bovine serum albumin (BSA, 5 mg/ml) followed by a 40 minutes incubation at room temperature with the primary antibody. After washing with DPBS, slides were incubated for 30 min with a secondary antibody and eventually rinsed with DPBS and air dried. Slides were mounted with Vectashield (Vector Laboratories). Primary antibodies were directed against epitopes for the inflammatory markers CD68 (macrophage) (refs.18,19; herein incorporated by reference in their entireties) MPO (neutrophil) (ref.20; herein incorporated by reference in its entirety) or the inflammation-related proteins IL1β, TNFα, IL-10, IL-13, CD206 (M2 macrophage) (refs.21-25; herein incorporated by reference in their entireties) and CD86 (M1 macrophage) (ref.26; herein incorporated by reference in its entirety). Antibodies directed against the ECM in regenerating bladder tissue (including COL4A$_3$ and fibronectin) were also utilized. Alexa Red 555 or FITC conjugated secondary antibodies (Molecular Probes) were utilized for visualization (ref.15; herein incorporated by reference in its entirety). Primary antibodies were utilized at dilutions ranging from 1:50 to 1:400, while secondary antibodies were utilized at a 1:400 dilution. All samples were additionally stained with 4',6-diamidino-2-phenylindole (DAPI; Sigma-Aldrich Corp.) to identify cells by nuclei visualization. Primary antibodies were purchased from Abcam or Santa Cruz Biotechnology.

Immunofluorescence quantification of stained tissue sections (including granuloma characterization) was carried out utilizing a Nikon Eclipse 50i microscope and Spot Advanced Imaging software. Ten images per animal were taken within the regenerating area of the bladder for any of the aforementioned inflammatory markers. The number of percent positive inflammatory cells was determined by manually counting marked/colored cells using ImageJ (National Institutes of Health) software. The cell counter plugin function was used to mark any cells expressing a given marker. The total number of cells were determined by opening DAPI alone images with ImageJ, and converting images into 8-bit grayscale. The threshold of the imaged was then adjusted to highlight all DAPI cells to be counted and the watershed setting was selected to separate any stacked/merged cells. Once desired cells were highlighted and separated, total cell counts were determined using the analyze particle tool, with size adjusted to 180 pixels-infinity and circularity set to 0.0-1.0.

Urodynamic Testing and Bladder Capacity Measurements of Augmented Bladders

The bladders of anesthetized athymic rats were exposed through the abdomen as previously described. A 20 gauge cannula (Becton Dickinson and Co.) was delicately placed into the bladder through the dome in order to obtain intravesical measurements. The cannula was connected to the Pump 11 Elite Syringe Pump (Harvard Apparatus) and to a physiological pressure transducer (SP844, MEMSCAP). The pressure transducer was connected to a bridge amplifier (Model FE221; AD Instruments). Continuous reading of the transvesical pressure was measured and plotted using LabChart 7.3 software (AD Instruments). The fill rate for each study ranged from 150-200 uL per minute. Bladder capacity was measured by a modified protocol (ref.13; herein incorporated by reference in its entirety). Sterile DPBS was injected into the bladder using a 27 gauge needle in 50 µl increments until fluid leakage was observed from the urethra of the animal. The total volume injected was then noted. This procedure was repeated at least three times per animal. Urine was evacuated from the bladder prior to the start of any bladder capacity measurements utilizing a sterile 27 gauge needle. Urodynamic and bladder capacity measurements were performed immediately prior to augmentation procedures and immediately prior to euthanization.

Statistical Analysis

Differences between control and treatment groups were determined using ANOVA with the Tukey-Kramer method for multiple comparisons (SAS 9.4). P<0.05 was considered statistically significant.

Example 2

Quantitative Morphometric and Histological Evaluation of SIS/AIF-PA Augmented Tissue The chemical structures of the AIF-PAs are provided (FIG. 6A-F). A representative scanning electron micrograph of an AIF-PA-coated small intestinal submucosa (SIS) scaffold reveals the high density of epitope-expressing nanofibers that stud the surface of the SIS scaffold (FIG. 6G). AIF-PAs 3-5 were used for 10 day time-point studies.

Figure 7:
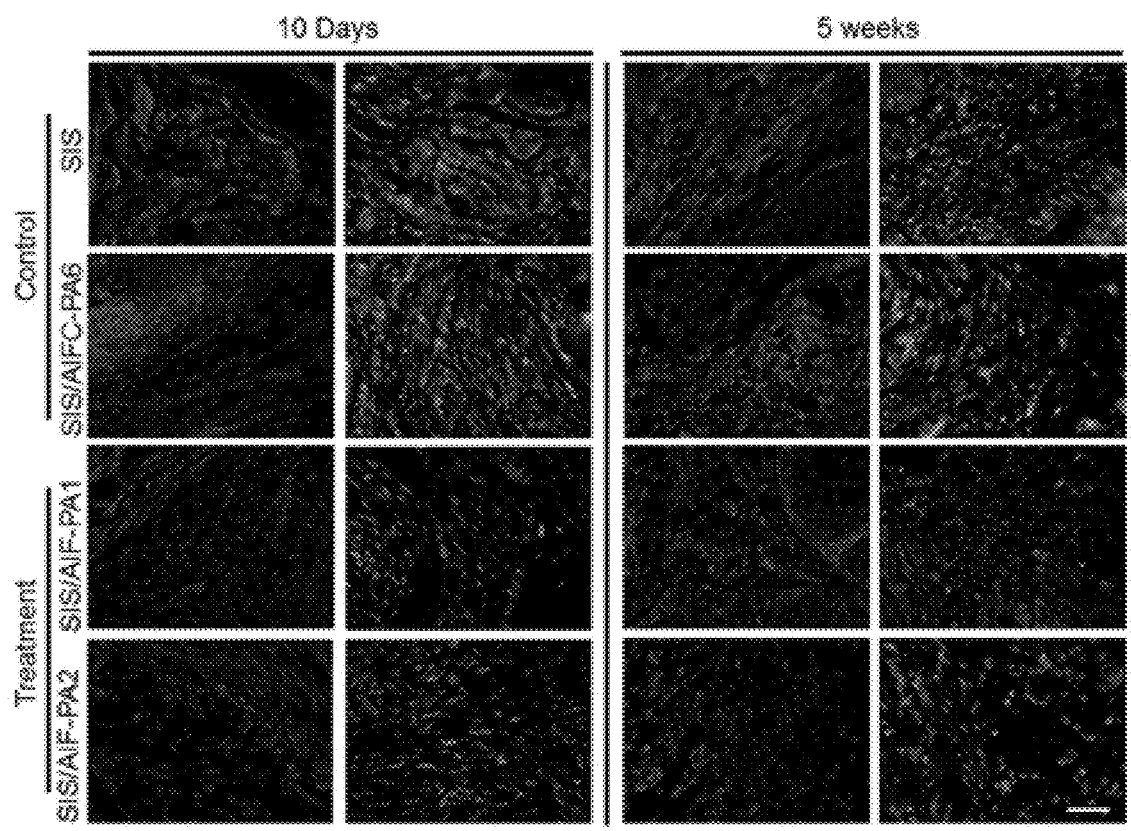
FIG. 7 shows extracellular matrix deposition amid regenerating bladder tissue. The accumulation of extracellular matrix in a localized tissue area can lead to the activation of fibrogenic pathways and decrease physiological function in a number of clinical pathologies (ref.46; herein incorporated by reference in its entirety). The examination of a collagen subtype and fibronectin was undertaken with control and treatment samples to determine additional sources of extracellular matrix deposition. Staining with antibodies against COL4A3, and fibronectin revealed heavy deposition of these extracellular matrices in control groups with a substantial decrease in treatment groups. Magnification 400× (Scale bar, 50 μm).
Figure 9:
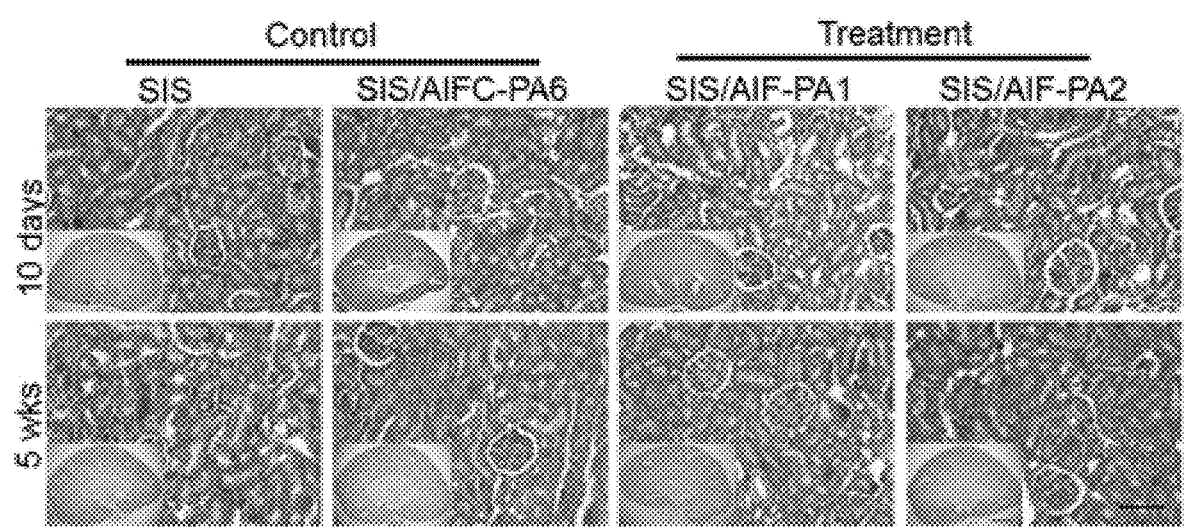
FIG. 9 shows gross and microscopic examination of kidneys from augmented animals. Histochemical staining of bladder tissue specimens was undertaken to determine whether there were any deleterious effects on the kidneys at the gross and microscopic levels following augmentation. At both the 10D and 5 W time-points, there appeared to be no detrimental effects related to the procedure in any of the conditions as determined by the Pathologist (M.D.H.). Microscopic images: magnification 200× (scale bar, 100 μm). Gross images: magnification 1× (Scale bar, 0.5 cm).

Masson's Trichrome (10 days and 5 weeks) staining of augmented bladder tissue specimens demonstrated varying levels of collagen accumulation in "control samples" (SIS alone and SIS/AIFC-PA6), respectively at 10 days post-augmentation. SIS augmented samples consistently demonstrated large and dense areas of collagen (depicted by black arrows; FIG. 1A; column I, row 1) accrued in a disorganized manner throughout the grafts mostly devoid of cells (red stain). Analogous results were also demonstrated with SIS/AIFC-PA6 (FIG. 1A; column I, row 2). In contrast, SIS/AIF-PA1 and SIS/AIF-PA2 ("treatment samples") exhibited lesser degrees of collagen and tissue was interspersed with encroaching cells from the native bladder (FIG. 1A; column I, rows 3 and 4). Other extracellular matrix tissue deposition was also examined (FIG. 7). H&E staining revealed high levels of infiltrating inflammatory cells in areas of regeneration in control samples (FIG. 1A; column II, rows 1 and 2; boxed areas). SIS samples further demonstrated the formation of granulation tissue throughout the graft as demonstrated by the dense staining seen in FIG. 1A (column II, row 1). Granulation tissue was evident in all samples but to a far lesser degree in treatment grafts at both time-points in both quantity and size (FIG. 8 and Table 1). The trend of collagen accumulation continued at the 5 week time-point as levels of collagen remained higher in control samples (FIG. 1A; column III, rows 1 and 2) and decreased with the treatment samples (FIG. 1A; column III, rows 3 and 4). Normal bladder architecture was also predominant in treatment grafts. Inflammatory cell populations were still present in control samples and were in limited number with treatment samples (FIG. 1A; column IV, rows 1-4). Kidney morphology appeared normal at the gross and microscopic levels (FIG. 9). Quantitative morphometric analyses of collagen and blood vessel formation revealed a disparity between control and treatment groups.

TABLE 1

Fewer granulomas were present in tissue from treatment groups, and granuloma size was decreased.
Control group tissue showed a greater total number of granulomas, a greater number of large granulomas
(>0.01 mm²), greater mean granuloma size, and greater maximum granuloma size. Granuloma number and size
decreased with time for all groups, but control groups continued to demonstrate higher number and greater size.

|  |  |  | Number of Granulomas | Number of Large Granulomas (>0.01 mm²) | Mean Granuloma Size (mm² × 1000) | Minimum Granuloma Size (mm² × 1000) | Maximum Granuloma Size (mm² × 1000) |
|---|---|---|---|---|---|---|---|
| 10D | Control | SIS | 11.00 ± 1.00 | 5.00 ± 1.00 | 18.15 ± 5.54 | 2.39 ± 0.86 | 70.67 ± 16.54 |
|  |  | SIS/AIFC-PA6 | 10.00 ± 1.00 | 6.00 ± 1.00 | 29.64 ± 0.74 | 5.12 ± 0.01 | 110.89 ± 1.51 |
|  | Treatment | SIS/AIF-PA1 | 4.00 ± 1.00 | 1.33 ± 0.33 | 8.77 ± 1.32 | 2.67 ± 0.15 | 23.39 ± 7.68 |
|  |  | SIS/AIF-PA2 | 4.00 ± 1.00 | 0.67 ± 0.33 | 5.95 ± 1.18 | 2.65 ± 0.17 | 11.99 ± 3.62 |
| 5W | Control | SIS | 6.25 ± 0.95 | 0.50 ± 0.29 | 5.91 ± 0.75 | 2.95 ± 0.32 | 10.94 ± 0.89 |
|  |  | SIS/AIFC-PA6 | 7.00 ± 1.08 | 1.00 ± 0.41 | 6.10 ± 0.51 | 2.21 ± 0.30 | 14.80 ± 2.30 |
|  | Treatment | SIS/AIF-PA1 | 1.75 ± 1.03 | 0 | 1.26 ± 0.88 | 0.97 ± 0.65 | 1.62 ± 1.15 |
|  |  | SIS/AIF-PA2 | 3.00 ± 1.00 | 0 | 3.00 ± 0.20 | 2.09 ± 0.39 | 4.08 ± 0.38 |

Figure 1B:
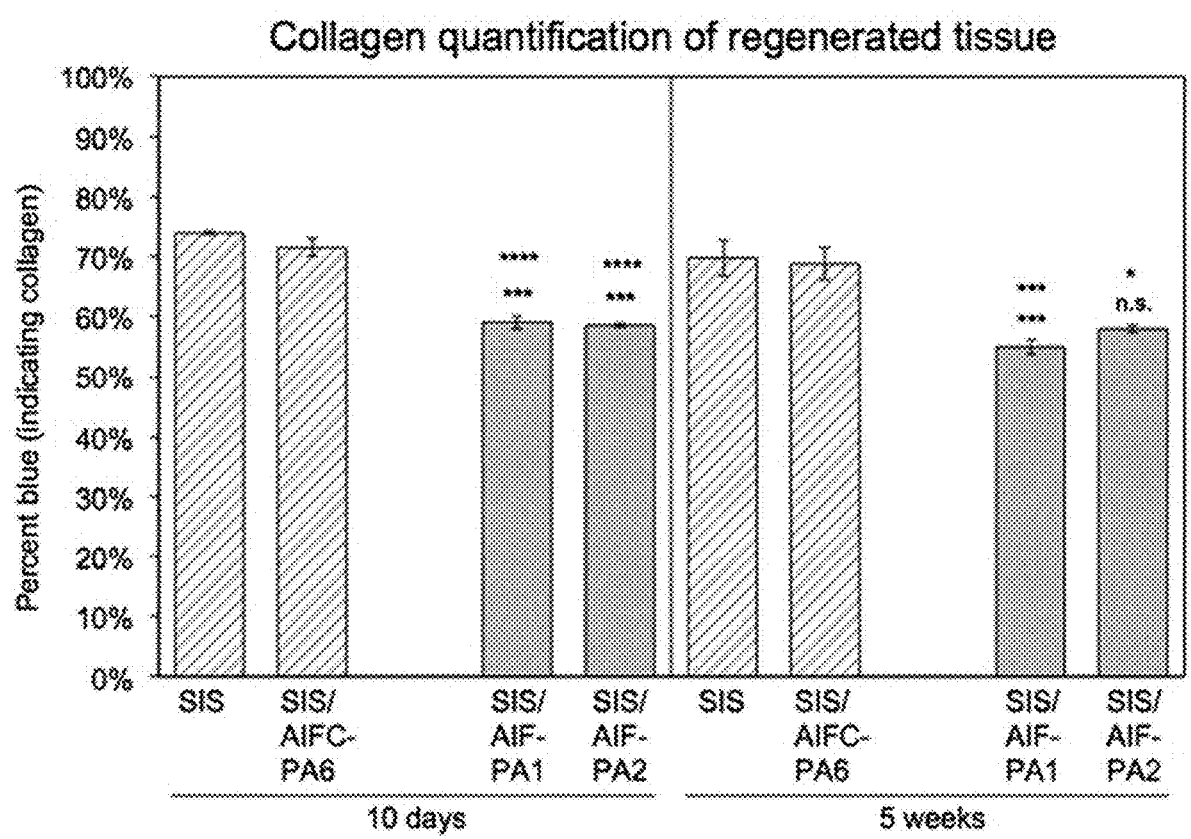
Figure 1C:
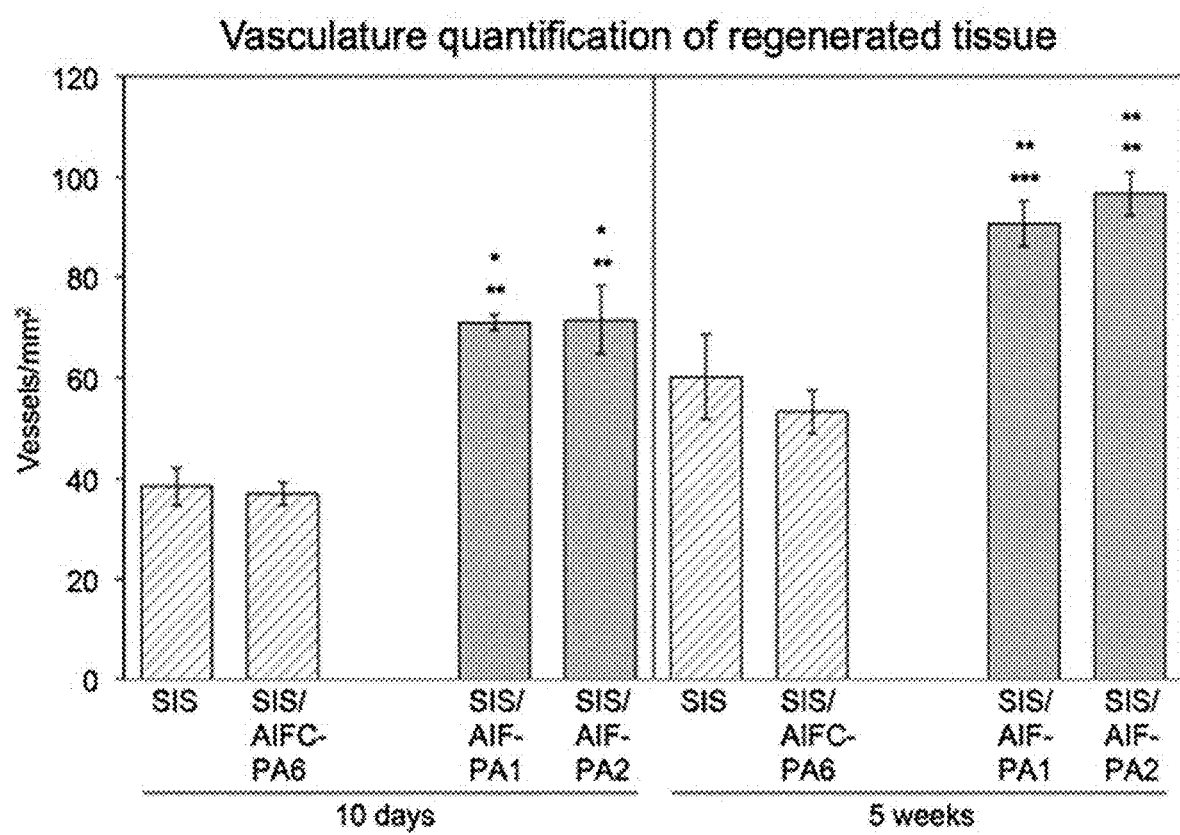
Figure 10:
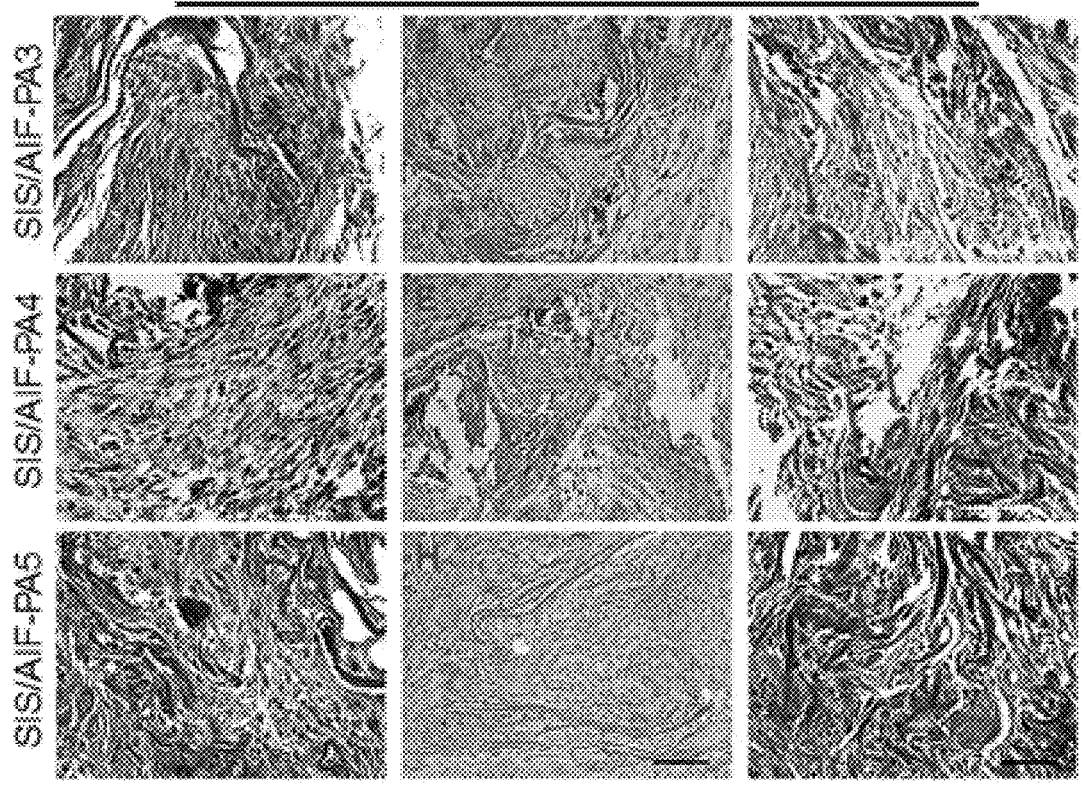
FIG. 10 shows histological characterization of SIS/AIF-PA augmented bladder tissue. Regenerated bladder tissue of AIF-PAs 3-5 treated SIS exhibited a similar distribution of collagen and native cell encroachment in regenerating tissue (A, D, G) as demonstrated by Masson's Trichrome staining. Collagen levels of SIS/AIF-PAs 3-5 were different than those compared to SIS/AIF-PAs 1-2 (see FIG. 15). H&E staining demonstrated inflammatory cell infiltrate (B, E, H) that was also greater than that found in SIS/AIF-PAs 1 and 2 treatment groups. Lastly, SIS/AIF-PA3 and SIS/AIF-PA4 composites demonstrated similar levels of blood vessel formation (C, F, arrows) while the SIS/AIF-PA5 treatment group demonstrated the least level of blood vessel formation in the regenerating bladder tissue. All data is based upon 10 day post-augmentation tissue samples. See FIG. 15 for quantified data based upon tissue imaging that includes collagen and blood vessel levels. Images are representative examples of multiple stained tissue samples. H&E images: magnification 200× (Scale bar; 100 μm). Trichrome images: magnification 400× (Scale bar; 50 μm).

The control groups exhibited mean levels of collagen approaching 70% (10D: SIS 73.9±0.2%, SIS/AIFC-PA6 71.5±1.4%; 5 W: SIS 69.8±3.0%, SIS/AIFC-PA6 68.8±2.7%) while samples in the treatment groups demonstrated mean levels of <60% (10D: SIS/AIF-PA1 59.1±1.1%, SIS/AIF-PA2 58.6±0.4%; 5 W: SIS/AIF-PA1 55.0±1.2%, SIS/AIF-PA2 58.0±0.6%) (FIG. 1B) At 5 weeks, none of the groups showed a significant increase or decrease from 10 day values. At 10 days post-augmentation, regenerated tissue in treatment group grafts was significantly more vascularized than in control group grafts (vessels/ mm², 10D: SIS 38.5±3.8, SIS/AIFC-PA6 37.0±2.3 vs. SIS/ AIF-PA1 71.0±1.5, SIS/AIF-PA2 71.5±6.7) (FIG. 1C). All groups demonstrated an increase in vessel number over time; mean levels for control groups at 5 weeks stayed below the mean levels for treatment groups at 10 days (vessels/ mm², 5 W: SIS 60.2±8.5, SIS/AIFC-PA6 53.3±4.4 vs. SIS/AIF-PA1 90.7±4.5, SIS/AIF-PA2 96.7±4.4) (FIG. 1C). Grafted samples SIS/AIF-PA3, SIS/AIF-PA4, and SIS/AIF-PA5 demonstrated differing degrees of collagen accumulation (FIG. 10, FIG. 15) and blood vessel formation (Fig. FIG. 10, FIG. 15) at 10 days post-augmentation. Bladder peripheral nerve regeneration was not apparent at either time-point under any treatment condition as determined by immunofluorescence staining. This may have been due to insufficient experimental duration.

Example 3

Evaluation of Inflammatory Cell Infiltrate of Grafted Bladder Tissue

Figure 2A:
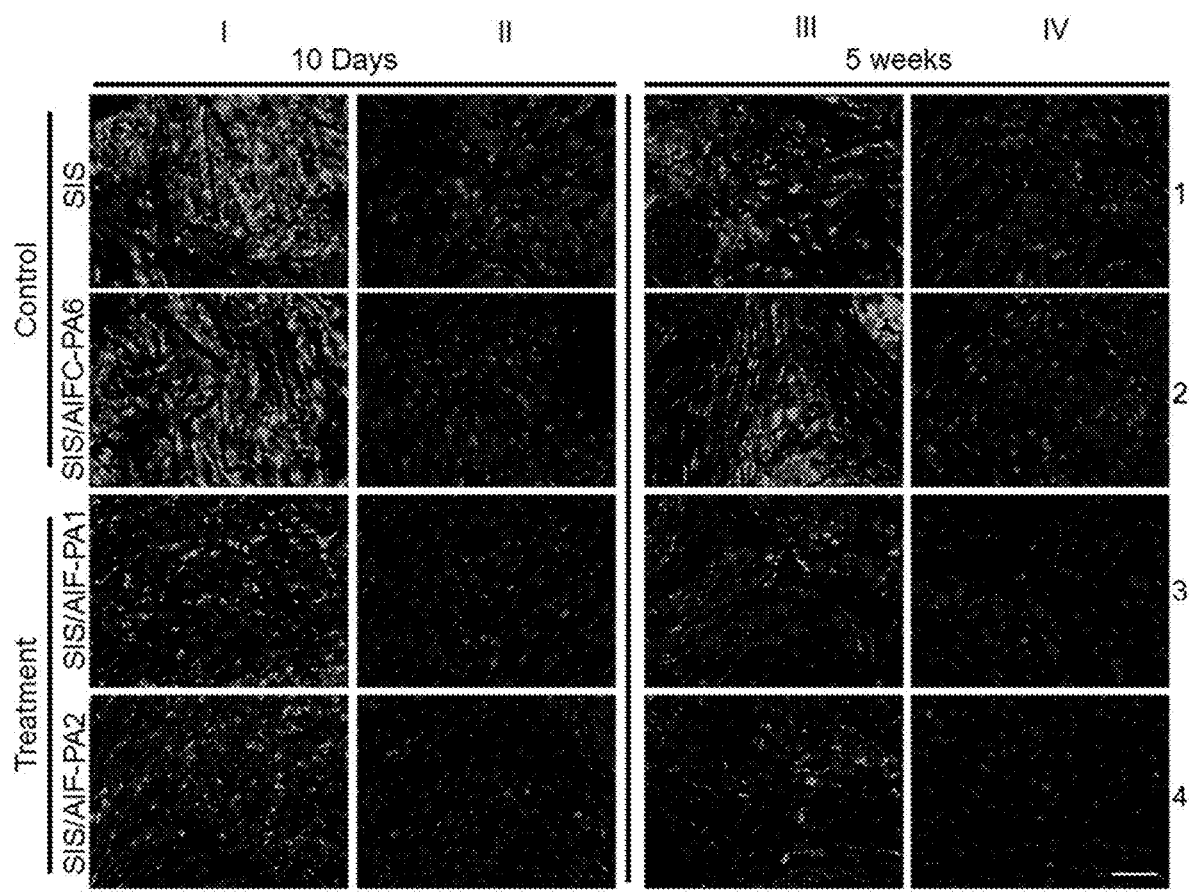
FIG. 2A-B shows innate immune cell distribution in regenerating bladder tissue. (A) Elevated levels of CD68+ macrophages and MPO+ neutrophils were evident in the control groups at the 10 day time-point. Although the levels of macrophage and neutrophil infiltrate decreased by 5 W, significant levels of both populations still presided in the tissues. Conversely, treatment groups demonstrated a significant decline in macrophage and neutrophil levels at both time-points compared to control groups. Magnification is 400× (scale bar, 50 μm). (B) Quantification of macrophages and neutrophils in augmented tissues demonstrated a marked decrease in both populations at 10D and 5 W in treatment groups. Data shown as means±SE. Significance shown for comparison of SIS/AIF-PA1 and SIS/AIF-PA2 to SIS (top) and SIS/AIFC-PA6 (bottom); **$P \leq 0.0001$, *$P < 0.001$.

Innate immune-derived cells are typically the first to arrive upon areas of tissue insult (ref.27; herein incorporated by reference in its entirety). The presence of macrophages and neutrophils was evaluated in both control and treatment grafts. CD68+ macrophages were highly abundant in control samples 10 days post-augmentation as evidenced by their intense staining (FIG. 2A; column I; rows 1 and 2). This staining encompassed the entirety of the graft especially along the sutured bladder perimeter at the juncture of the SIS and the native bladder tissue. This was accompanied by a localized influx of numerous MPO+ (myeloperoxidase) neutrophils (FIG. 2A; column II; rows 1 and 2) to a lesser degree than macrophages, again spanning the entirety of the graft. In contrast, treatment groups qualitatively demonstrated markedly reduced levels of both cell types (FIG. 2A; columns I and II; rows 3 and 4). Although the macrophage level decreased from the 10 day to 5 week time-point, there were still significant levels of CD68+ macrophages present throughout the graft in control samples (FIG. 2A; column III; rows 1 and 2) and this was decreased in treatment groups (FIG. 2A; column III; rows 3 and 4). This trend of inflammatory cell reduction was also seen with levels of MPO+ neutrophils but was still greatest in both control graft samples (FIG. 2A; column IV; rows 1-4).

Figure 2B:
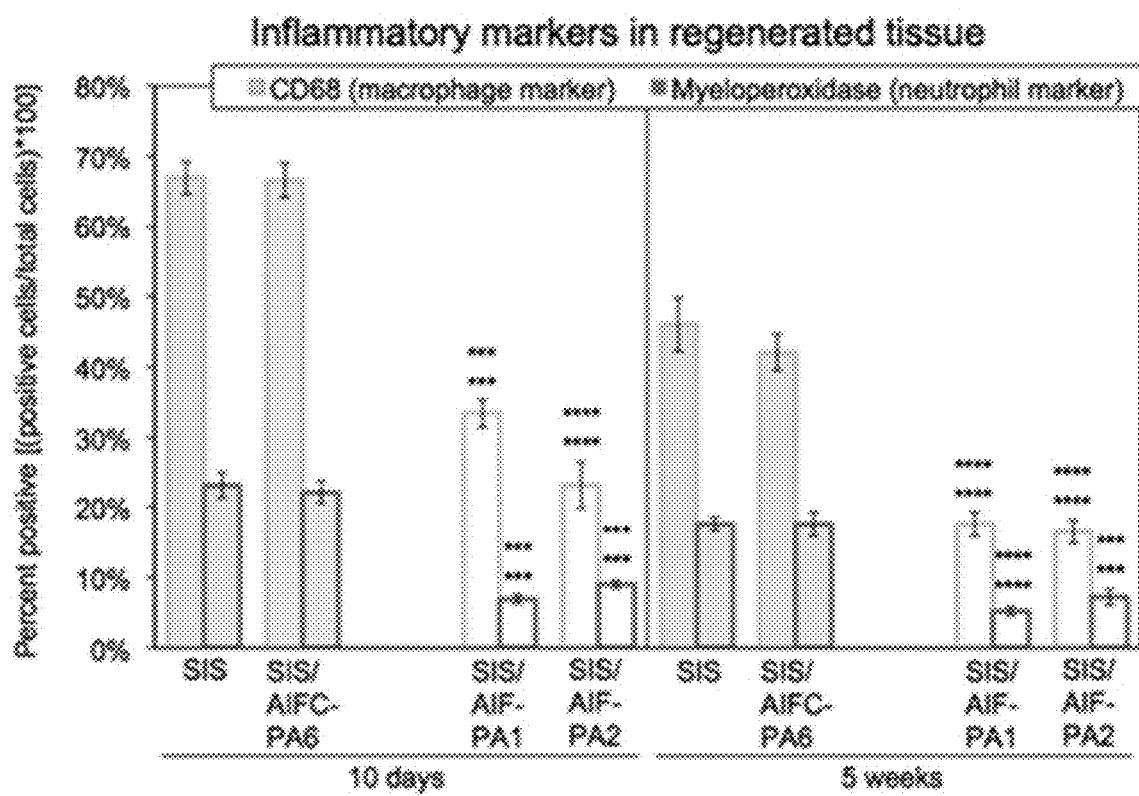
Figure 11:
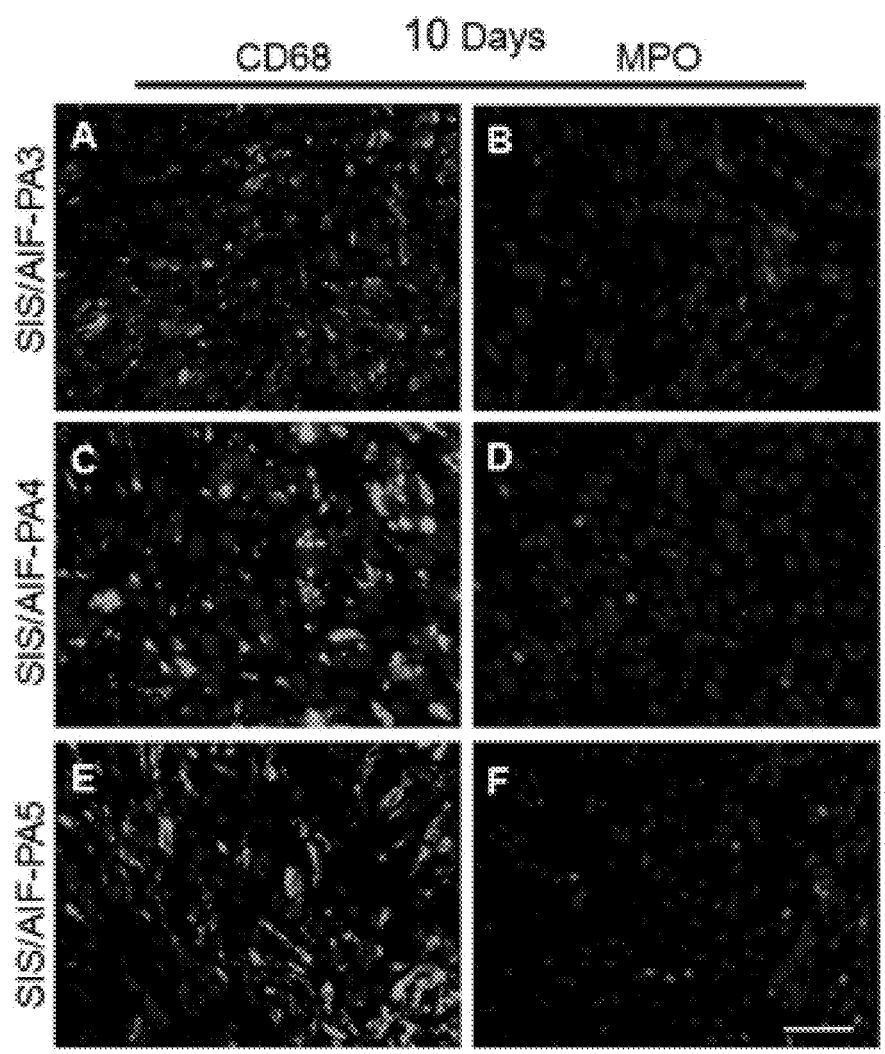
FIG. 11 shows inflammatory cell distribution in SIS/AIF-PAs 3-5 augmented bladder tissue. Immunofluorescence imaging demonstrated the presence of $CD68^+$ macrophages at high levels in SIS/AIF-PA5 tissues (Panel E) while SIS/AIF-PA3 and SIS/AIF-PA4 revealed similar levels of macrophages (Panel A,C), reduced to SIS/AIF-PA5. Similarly, the presence of $MPO^+$ neutrophils was slightly higher in the SIS/AIF-PA5 treated group (Panel F) as compared to SIS/AIF-PA3 and SIS/AIF-PA4 treatment groups. Overall, SIS/AIF-PA3 treatment groups had comparable macrophage levels to SIS/AIF-PA1 but elevated neutrophil counts. SIS/AIF-PA5 had the worst overall counts of examined inflammatory cells compared to all other treatment groups. All data is based upon 10D post-augmentation tissue samples. See FIG. 16 for quantified data based upon tissue imaging. Images are representative examples of multiple stained tissue samples. DAPI=blue. Magnification 400× (Scale bar, 50 μm).

Quantitative characterization of macrophage and inflammatory markers in control and treatment samples was additionally evaluated. At 10 days post-augmentation, >60% of cells in regenerated tissue from control groups were CD68+. Separately, >20% of cells stained positive for MPO and significantly lower mean positive percentages were detected in tissue from treatment groups (CD68: SIS/AIF-PA1 33.4±2.0%, SIS/AIF-PA2 23.1±3.3%; MPO: SIS/AIF-PA1 6.9±0.7%, SIS/AIF-PA2 9.0±0.5%) (FIG. 2B). By 5 weeks, mean positive percentages for CD68 and MPO in control group tissue were reduced (CD68: SIS 46.0±3.9%, SIS/ AIFC-PA6 42.0±2.6%; MPO: SIS 17.6±1.0%, SIS/AIFC-PA6 17.6±1.8%), but remained higher than levels in treatment group tissue (CD68: SIS/AIF-PA1 17.6±1.8%, SIS/ AIF-PA2 16.5±1.6%; MPO: SIS/AIF-PA1 5.2±0.7%, SIS/ AIF-PA2 7.2±1.1%)(FIG. 2B). SIS/AIF-PA3, SIS/AIF-PA4, and SIS/AIF-PA5 grafted samples demonstrated differing degrees of inflammatory cellular infiltrate at the 10 day time-point only (FIG. 11, FIG. 16).

Example 4

Macrophage Subtype Distribution in Regenerating Bladder Tissue

Macrophage populations, including the M1 and M2 phenotypic subtypes, have the capacity to either promote or deter proper tissue regeneration (ref.28; herein incorporated by reference in its entirety). FIG. 3A (columns I and II, rows 1 and 3) demonstrates dense immunofluorescence staining with CD86 (a M1 macrophage marker (ref.26; herein incorporated by reference in its entirety)) in both control groups at 10 days and 5 weeks post-augmentation, respectively, in regenerating bladder tissue. This observation is quite contrary to the treatment groups where there is a paucity of CD86+ macrophages (columns III and IV, rows 1 and 3) specifically at the 5 week time-points. Further immunofluorescence staining with CD206 (a M2 macrophage marker (ref.16; herein incorporated by reference in its entirety))

indicates the decreased presence of CD206⁺ macrophages at the 10 day time-point (columns I-IV; row 2) in all groups.

Figure 3B:
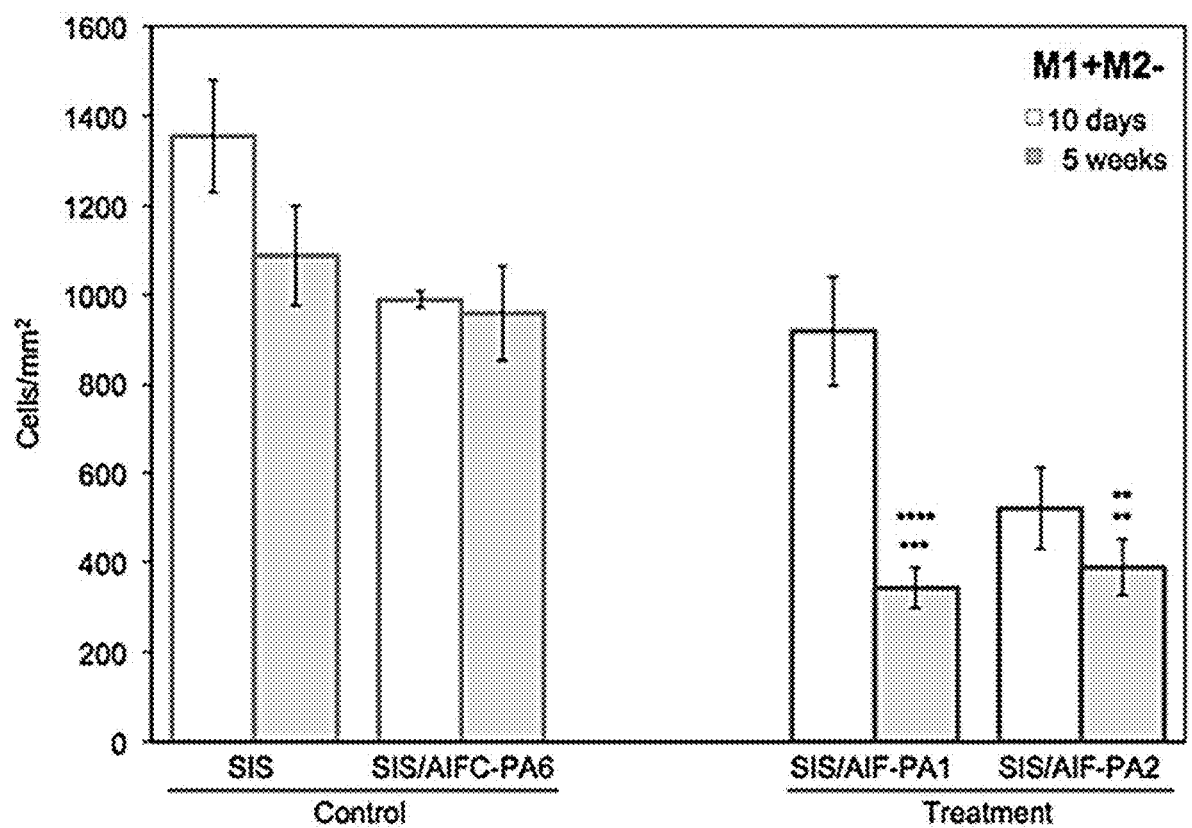
Figure 3C:
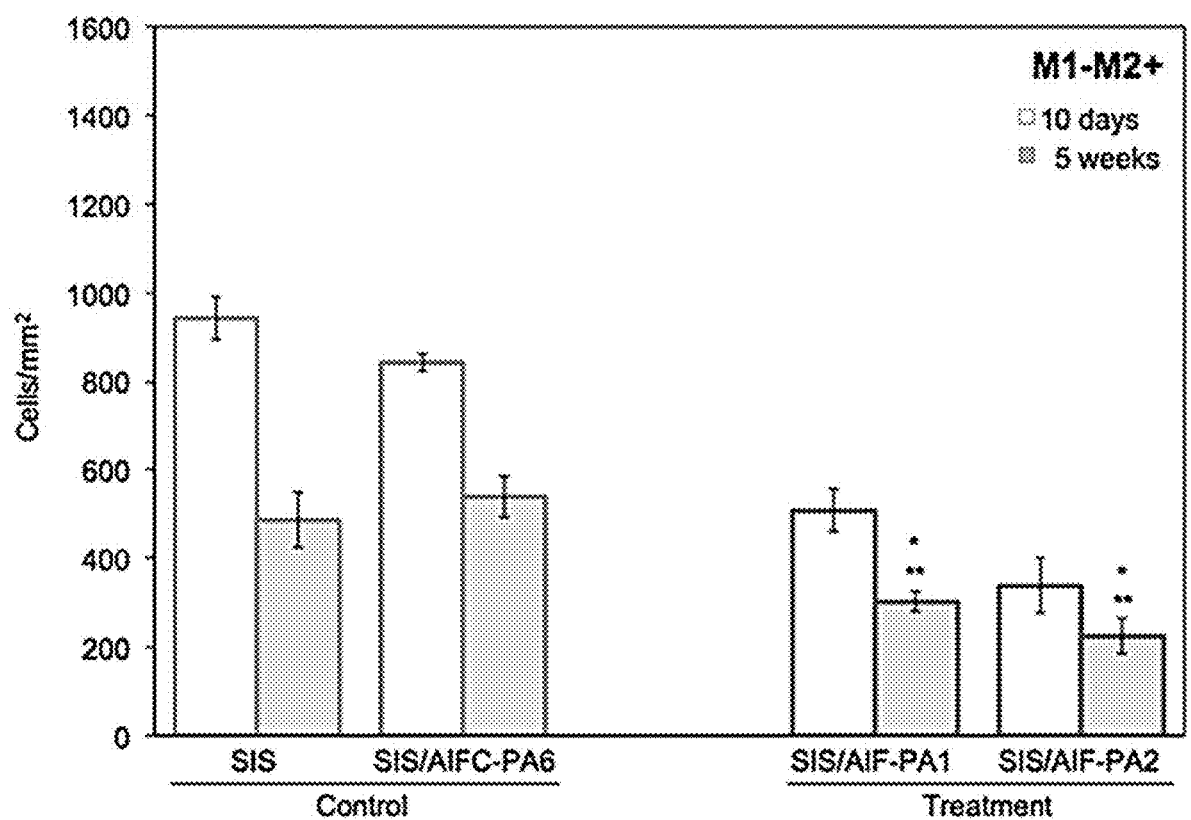

Assessment of shifts in $M1^+M2^-$ (termed "M1") and $M1^-M2^+$ (termed "M2") macrophage subsets from 10 days to 5 weeks demonstrated a substantial reduction in the number of M2, but not M1, cells in both control groups (M2: (10D) SIS 942.3±49.1, SIS/AIFC-PA6 842.5±18.9 vs. (5 W) SIS 486.9±61.2, SIS/AIFC-PA6 539.3±46.7. M1: (10D) SIS 1354.1±125.4, SIS/AIFC-PA6 986.9±18.1 vs. (5 W) SIS 1087.1±113.7, SIS/AIFC-PA6 957.7±106.2; cells/mm$^2$) (FIG. 3B). Continued elevation of M1 cell numbers was not evident in treatment groups. Mean levels of both M1 and M2 subpopulations were significantly lower than control group levels ((5 W), M1: SIS/AIF-PA1 343.4±45.4, SIS/AIF-PA2 389.4±62.6. M2: SIS/AIF-PA1 301.7±23.0, SIS/AIF-PA2 224.7±39.0; cells/mm$^2$) (FIG. 3C). Specifically, M1 levels dropped considerably in the SIS/AIF-PA1 group from 10 days to 5 weeks while M2 levels were lower at 10 days and further decreased by 5 weeks. Comparatively low numbers of M1 and M2 cells were detected in the SIS/AIF-PA2 group at 10 days and remained low at 5 weeks.

Figure 12:
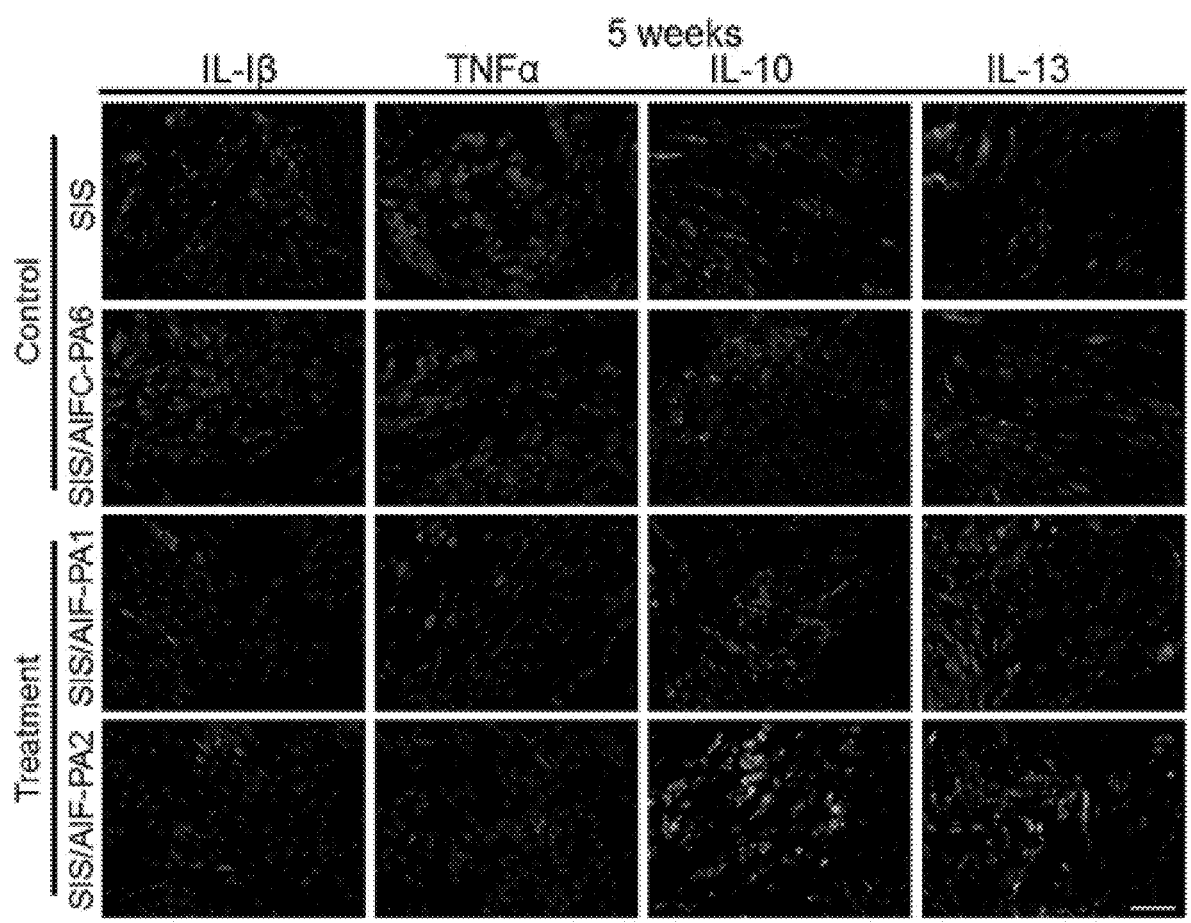
FIG. 12 shows 5 week cytokine expression in augmented bladder tissue. Levels of both pro- (IL-1β and TNFα) and anti-inflammatory (IL-10 and IL-13) cytokines were reduced in all groups compared to 10 day treatment samples. However, IL-1β and TNFα were still elevated in control groups as compared to treatment groups. The converse was true of IL-10 and IL-13 expression where the treatment groups demonstrated moderately higher levels of cytokine expression as compared to the control groups. See Table 2 for quantified cytokine expression data. Magnification 400× (Scale bar, 50 μm).

Distinct, antithetical cytokine profiles were apparent for control and treatment groups (FIG. 4B). At 10 days post-augmentation, control group graft tissue (SIS and SIS/AIFC-PA6, respectively) showed high levels of pro-inflammatory cytokines IL-1β and TNFα, with low levels of anti-inflammatory cytokines IL-10 and IL-13 (IL-1β: 56.7±5.0%, 63.3±2.4%; TNFα: 63.1±2.6%, 65.1±5.1%; IL-10: 22.0±2.6%, 27.8±3.0%; IL-13: 24.8±2.5%, 28.6±3.0%). In contrast, treatment group graft tissue (SIS/AIF-PA1 and SIS/AIF-PA2, respectively) showed decreased levels of IL-1β and TNFα, with elevated IL-10 and IL-13 expression (IL-1β: 28.2±2.4%, 21.2±2.4%; TNFα: 32.8±2.5%, 26.3±2.5%; IL-10: 52.0±3.1%, 56.2±3.4%; IL-13: 48.2±2.8%, 41.2±2.2%) (FIG. 4B). A decrease in cytokine expression by 5 weeks was noted but the overall cytokine profiles remained the same in that higher IL-1β and TNFα for control groups, and higher IL-10 and IL-13 for treatment groups was observed (FIG. 12, Table 2). Cytokine expression levels of SIS/AIF-PAs 3-5 augmented tissues were not determined at 10 day or 5 week time-points.

TABLE 2

At 5 weeks post-augmentation, control and treatment groups maintained their contrasting cytokine profiles. Control group graft tissue continued to be characterized by higher expression of pro-inflammatory cytokines IL-1β and TNFα (mean positive levels > 40%), with lower levels of anti-inflammatory cytokines IL-10 and IL-13. Expression levels of pro-inflammatory cytokines IL-1β and TNFα were significantly lower in graft tissue from treatment groups (mean positive levels < 20%), and pro-inflammatory cytokine expression was lower than anti-inflammatory cytokine expression for these groups. Data shown as means ± SE. Significance shown for comparison of treatment groups SIS/AIF-PA3, SIS/AIF-PA4 and SIS/AIF-PA5 to control groups SIS (left) and SIS/AIFC-PA6 (right); **$P ≤ 0.0001$, *$P < 0.001$, **$P < 0.01$, *$P < 0.05$, n.s. = non-significant.

| Cytokine expression (shown as percentage of cells staining positive) | | Pro-inflammatory | | Anti-inflammatory | |
|---|---|---|---|---|---|
| | | IL-1β | TNFα | IL-10 | IL-13 |
| Control | SIS | 42.0 ± 1.8 | 47.3 ± 3.4 | 18.3 ± 2.7 | 16.6 ± 2.1 |
| | SIS/AIFC-PA6 | 42.9 ± 1.8 | 42.8 ± 2.2 | 21.1 ± 2.1 | 20.4 ± 2.6 |
| Treatment | SIS/AIF-PA1 | 12.9 ± 2.0 **/ | 17.4 ± 2.9 /* | 30.0 ± 1.6 */n.s. | 26.1 ± 2.7 n.s./n.s. |
| | SIS/AIF-PA2 | 11.5 ± 2.7 **/ | 14.8 ± 1.7 / | 33.2 ± 2.3 /* | 32.0 ± 1.8 **/* |

Example 5

Expression of Inflammation-Modulating Cytokines in Regenerated Bladder Tissue

Pro- and anti-inflammatory cytokines possess the ability to greatly influence tissue remodeling with both positive and negative outcomes (refs.28,29; herein incorporated by reference in their entireties). The expression of pro-inflammatory cytokines IL-1β and TNFα was most abundant in control groups (FIG. 4A columns I and II; rows 1 and 2) and encompassed the entirety of the graft at the 10 day time-point. In complete contrast, treatment groups exhibited dramatically lesser levels of the aforementioned cytokines at the same time-point (FIG. 4A columns I and II; rows 3 and 4). The anti-inflammatory cytokines IL-10 and IL-13 appeared along an expression spectrum amongst groups. Augmented control groups expressed a paucity of these cytokines while treatment groups tended to have a greater localized expression in regenerating bladder tissue (FIG. 4A columns III and IV; rows 3 and 4) 10 days post-augmentation.

Regenerated tissue was also examined for the percentage of cells staining positive for the aforementioned cytokines.

Example 6

Physiological Bladder Testing

Figure 5:
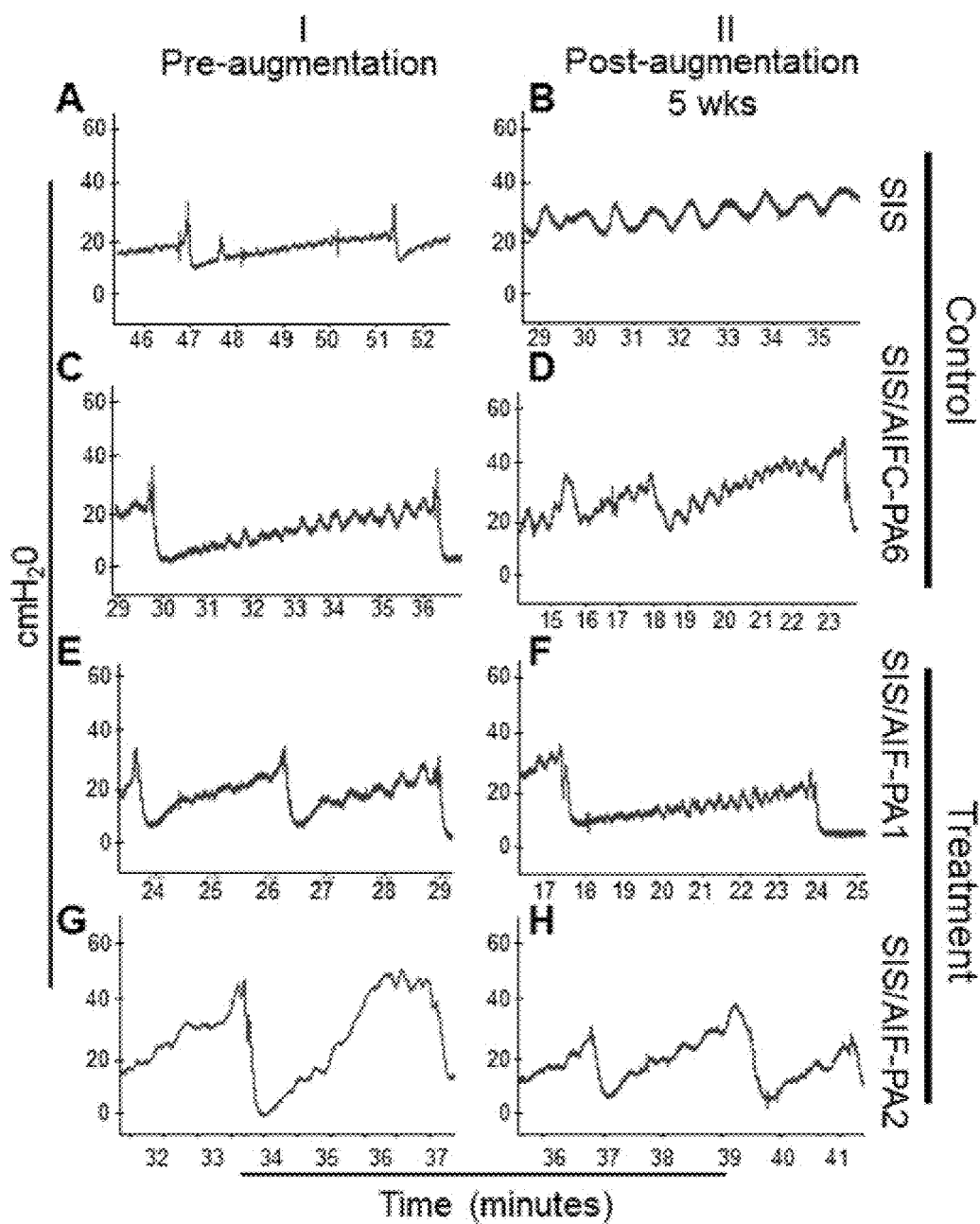
FIG. 5 shows urodynamic studies. UDS testing provided physiological bladder data in the form of bladder pressures and voiding patterns. A similar pattern of bladder filling/voiding was observed amongst animals in the pre-augmentation group (panels A, C, E, G). Decreased bladder compliance was observed in the control groups post-augmentation (panels B, D) while SIS/AIF-PA1 led to higher bladder compliance and decreased intravesical pressures (panel F). SIS/AIF-PA2 treated animals exhibited improved bladder compliance accompanied by a very modest decrease in bladder intravesical pressure (panel H).

Bladders underwent urodynamic testing (UDS) pre- and post-augmentation. Bladders were gradually filled with sterile saline until a bladder contraction occurred. Bladder pressures rose during the filling until bladder contractions occurred at intravesical pressures of 30-40 cm H$_2$O (FIG. 5, panels A, C, E, and G). This was similar for the SIS group, SIS/AIF-PA1, SIS/AIF-PA2, and SIS/AIFC-PA6 groups. Bladder augmentation with SIS alone led to no change in voiding pressures and decreased bladder compliance (decreased filling time until voiding occurred, panel B). This was similar for SIS/AIFC-PA6 in which the voiding pressures were unchanged or even slightly elevated (panel D). In contrast, augmentation with SIS/AIF-PA1 led to a decrease in intravesical pressures during voiding to approximately 25 cm H$_2$O (35 cm H$_2$O before augmentation) combined with higher bladder compliance as the prolonged filling duration shows (panel F). In animals augmented with SIS/AIF-PA2, the slope of pressure increase was also decreased indicating an improved compliance and we observed a decrease in bladder pressure during voiding as well (approximately 35 cm H₂O compared to 45 cmH₂O before augmentation). In contrast to the above, augmentation with SIS alone and augmentation with SIS/AIF-PA2 was not associated with an increase in bladder compliance or a decreased maximum pressure. Percent bladder capacity recovery was also measured (Table 3).

TABLE 3

Bladder capacity was measured pre-surgery and at 5 weeks post-augmentation; percent recovery (shown as means ± SE) was calculated as ((5-week capacity − pre-surgery capacity) * 100). Mean values were similar for control and treatment groups, and indicated full recovery of capacity by 5 weeks. Bladders were further examined at this time-point for presence of stones. In control groups, >30% of animals formed stones. Stones were found in a lower percentage of animals in the treatment groups. It has been demonstrated that there is a correlation between macrophage pro- and anti-inflammatory cytokine expression and stone formation (ref.53; herein incorporated by reference in its entirety).

|  |  | Bladder Capacity Recovery (%) | Bladder Stone Formation (shown as percentage of animals forming stones) |
|---|---|---|---|
| Control | SIS | 107.8 ± 2.5 | 33.3 |
|  | SIS/AIFC-PA6 | 105.4 ± 5.1 | 42.9 |
| Treatment | SIS/AIFC-PA1 | 112.1 ± 3.3 | 25.0 |
|  | SIS/AIFC-PA2 | 104.4 ± 6.7 | 16.7 |

REFERENCES

The following references, some of which are references above by number (e.g., (ref.X)), are herein incorporated by reference in their entireties.
(1) Montesano R, Orci L. Transforming growth factor beta stimulates collagen-matrix contraction by fibroblasts: implications for wound healing. Proc Natl Acad Sci USA. 1988; 85; 4894-7.
(2) Velnar T, Bailey T, Smrkolj V. The wound healing process: an overview of the cellular and molecular mechanisms. J Int Med Res. 2009; 37; 1528-42.
(3) Oberpenning F, Meng J, Yoo J J, Atala A. De novo reconstitution of a functional mammalian urinary bladder by tissue engineering. Nat Biotechnol 1999; 17; 149-55.
(4) Tili E, Michaille J J, Wernicke D, Alder H, Costinean S, Volinia S, et al. Mutator activity induced by microRNA-155 (miR-155) links inflammation and cancer. Proc Natl Acad Sci USA. 2011; 108; 4908-13.
(5) Serhan C N, Savill J. Resolution of inflammation: the beginning programs the end. Nat Immunol. 2005; 6; 1191-97.
(6) ten Broek R P, Issa Y, van Santbrink E J, Bouvy N D, Kruitwagen R F, Jeekel J, et al. Burden of adhesions in abdominal and pelvic surgery: systematic review and met-analysis. BMJ 2013; 347; f5588-f5603.
(7) Datta A, Scotton C J, Chambers R. Novel therapeutic approaches for pulmonary fibrosis. Br J Pharmacol 2011; 163; 141-72.
(8) Hartgerink J D, Beniash E, Stupp S I. Self-assembly and mineralization of peptide-amphiphile nanofibers. Science 2001; 294; 1684-88.
(9) Webber M J, Tongers J, Newcomb C J, Marquardt K T, Bauersachs J, Losordo D W, et al. Supramolecular nanostructures that mimic VEGF as a strategy for ischemic tissue repair. Proc Natl Acad Sci USA. 2011; 108; 13438-443.
(10) Silva G A, Czeisler C, Niece K L, Beniash E, Harrington D A, Kessler J A, et al. Selective differentiation of neural progenitor cells by high-epitope density nanofibers. Science 2004; 303; 1352-55.
(11) Sohn J, Kim T I, Yoon Y H, Kim J Y, Kim S Y. Novel transglutaminase inhibitors reverse the inflammation of allergic conjunctivitis. J Clin Invest. 2003; 111; 121-28.
(12) Ashley R A, Palmer B W, Schultz A D, Woodson B W, Roth C C, Routh J C, et al. Leukocyte inflammatory response in a rat urinary bladder regeneration model using porcine small intestinal submucosa scaffold. Tissue Eng Part A 2004; 15; 3241-46.
(13) Sharma A K, Bury M I, Marks A J, Fuller N J, Meisner J W, Tapaskar N, et al. A nonhuman primate model for urinary bladder regeneration using autologous sources of bone marrow-derived mesenchymal stem cells. Stem Cells 2011; 29; 241-50.
(14) Miele L, Cordella-Miele E, Mantile G, Peri A, Mukherjee A B Uteroglobin and uteroglobin-like proteins: the uteroglobin family of proteins. J Endocrinol Invest. 1994; 17; 679-92.
(15) Sharma A K, Bury M I, Fuller N J, Marks A J, Kollhoff D M, Rao M V, et al. Cotransplantation with specific populations of spina bifida bone marrow stem/progenitor cells enhances urinary bladder regeneration. Proc Natl Acad Sci USA 2013; 110; 4003-8.
(16) Ashley R A, Roth C C, Palmer B W, Kibar Y, Routh J C, Fung K M, et al. Regional variations in small intestinal submucosa evoke differences in inflammation with subsequent impact on tissue regeneration in the rat bladder augmentation model. BJU Int 2010; 105; 1462-68.
(17) Sharma A K, Hota P V, Matoka D J, Fuller N J, Jandali D, Thaker H, et al. Urinary bladder smooth muscle regeneration utilizing bone marrow derived mesenchymal stem cell seeded elastomeric poly(1,8-octanediol-co-citrate) based thin films. Biomaterials 2010; 31; 6207-17.
(18) Kempf W, Adams V, Wey N, Moos R, Schmid M, Avitabile E, et al. CD68+ cells of monocyte/macrophage lineage in the environment of AIDS-associated and classic-sporadic Kaposi sarcoma are singly or doubly infected with human herpesviruses 7 and 6B. Proc Natl Acad Sci USA. 1997; 94; 7600-5.
(19) Khare S, Ratsimandresy R A, de Almeida L, Cuda C M, Rellick S L, Misharin A V, et al. The PYRIN domain-only protein POP3 inhibits ALR inflammasomes and regulates responses to infection with DNA viruses. Nat Immunol 2014 Epub ahead of print.
(20) Hazen S L, d'Avignon A, Anderson M M, Hsu F F, Heinecke J W. Human neutrophils employ the myeloperoxidase-hydrogen peroxide-chloride system to oxidize alpha-amino acids to a family of reactive aldehydes. Mechanistic studies identifying labile intermediates along the reaction pathway. J Biol Chem 1998; 273; 4997-05.
(21) Hernández-Rodríguez J, Segarra M, Vilardell C, Sánchez M, García-Martinez A, Esteban M J, et al. Tissue

(21) production of pro-inflammatory cytokines (IL-1beta, TNFalpha and IL-6) correlates with the intensity of the systemic inflammatory response and with corticosteroid requirements in giant-cell arteritis. Rheumatology 2004; 43; 294-301.

(22) Gessner A, Mohrs K, Mohrs M. Mast cells, basophils, and eosinophils acquire constitutive IL-4 and IL-13 transcripts during lineage differentiation that are sufficient for rapid cytokine production. J Immunol 2005; 174; 1063-72.

(23) Hawkes C A, McLaurin J. Selective targeting of perivascular macrophages for clearance of beta-amyloid in cerebral amyloid angiopathy. Proc Natl Acad Sci USA. 2009; 106; 1261-66.

(24) Souza K L, Gurgul-Convey E, Elsner M, Lenzen S. Interaction between pro-inflammatory and anti-inflammatory cytokines in insulin-producing cells. J Endocrinol 2008; 197; 139-50.

(25) Murray P J. The primary mechanism of the IL-10-regulated antiinflammatory response is to selectively inhibit transcription. Proc Natl Acad Sci USA. 2005; 102; 8686-691.

(26) Kigerl K A, Gensel J C, Ankeny D P, Alexander J K, Donnelly D J, Popovich P G., et al. Identification of two distinct macrophage subsets with divergent effects causing either neurotoxicity or regeneration in the injured mouse spinal cord. J Neurosci 2009; 29; 13435-444.

(27) Diegelmann R F, Evans M. C. Wound healing: an overview of acute, fibrotic and delayed healing. Front Biosci 2004; 9; 283-89.

(28) Galli S J, Borregaard N, Wynn T A. Phenotypic and functional plasticity of cells of innate immunity: macrophages, mast cells and neutrophils. Nat Immunol 2011; 12; 1035-44.

(29) Mantovani A, Biswas S K, Galdiero M R, Sica A, Locati M. Macrophage plasticity and polarization in tissue repair and remodelling. J Pathol 2013; 229; 176-85.

(30) Malik A F, Hoque R, Ouyang X, Ghani A, Hong E, Khan K, et al. Inflammasome components Asc and caspase-1 mediate biomaterial-induced inflammation and foreign body response. Proc Natl Acad Sci USA 2011; 108; 20095-100.

(31) Vacanti N M, Cheng H, Hill P S, Guerreiro J D, Dang T T, Ma M, et al. Localized delivery of dexamethasone from electrospun fibers reduces the foreign body response. Biomacromolecules 2012; 13; 3031-3038.

(32) Fujii T, Fuchs B C, Yamada S, Lauwers G Y, Kulu Y, Goodwin J M, et al. Mouse model of carbon tetrachloride induced liver fibrosis: Histopathological changes and expression of CD133 and epidermal growth factor. BMC Gastroenterol 2010; 10; 79-89.

(33) Gurtner G C, Werner S, Barrandon Y, Longaker M T. Wound repair and regeneration. Nature 2008; 453; 314-21.

(34) Caione P, Capozza N, Zavaglia D, Palombaro G, Boldrini R. In vivo bladder regeneration using small intestinal submucosa: experimental study. Pediatr Surg Int 2006; 22; 593-99.

(35) Slaughenhoupt B L, Mathews R I, Peppas D S, Gearhart J P. A large animal model of bladder exstrophy: observations of bladder smooth muscle and collagen content. J Urol 1999; 162; 2119-122.

(36) Tang L, Eaton J W. Inflammatory responses to biomaterials. Am J Clin Pathol 1995; 103, 466-71.

(37) Ryden L, Molnar D, Esposito M, Johansson A, Suska F, Palmquist A, et al. Early inflammatory response in soft tissues induced by thin calcium phosphates. J Biomed Mater Res A 2103; 101; 2712-17.

(38) Cu A, Ye Q, Sarria R, Nakamura S, Guzman J, Costabel U. N-acetylcysteine inhibits TNF-alpha, sTNFR, and TGF-beta1 release by alveolar macrophages in idiopathic pulmonary fibrosis in vitro. Sarcoidosis Vasc Diffuse Lung Dis 2009; 26; 147-54.

(39) Zhang Y, Lee T C, Guillemin B, Yu M C, Rom W N. Enhanced IL-1 beta and tumor necrosis factor-alpha release and messenger RNA expression in macrophages from idiopathic pulmonary fibrosis or after asbestos exposure. J Immunol 1993; 150; 4188-96.

(40) Bongartz T, Sutton A J, Sweeting M J, Buchan I, Matteson E L, Montori V. Anti-TNF antibody therapy in rheumatoid arthritis and the risk of serious infections and malignancies: systematic review and meta-analysis of rare harmful effects in randomized controlled trials. JAMA 2006; 295; 2275-85.

(41) Chen K, Wei Y, Sharp G C, Braley-Mullen H. Decreasing TNF-alpha results in less fibrosis and earlier resolution of granulomatous experimental autoimmune thyroiditis. J Leukoc Biol 2007; 81; 306-14.

(42) Dinarello C A, van der Meer J W. Treating inflammation by blocking interleukin-1 in humans. Semin Immunol 2013; 25; 469-84.

(43) Gerridzen R G, Thijssen A M, Dehoux E. Risk factors for upper tract deterioration in chronic spinal cord injury patients. J Urol 1992; 147; 416-18.

(44) Zuo L, Tozawa K, Okada A, Yasui T, Taguchi K, Ito Y, et al. A paracrine mechanism involving renal tubular cells, adipocytes and macrophages promotes kidney stone formation in a simulated metabolic syndrome environment. J Urol 2014

(45) Roupé K M, Nybo M, Sjobring U, Albertus P, Schmidtchen A, Sorensen O E. Injury is a major inducer of epidermal innate immune responses during wound healing. J Invest Dermatol 2010; 130; 1167-77.

(46) Wynn T A. Common and unique mechanisms regulate fibrosis in various fibroproliferative diseases. J Clin Invest 2007; 117; 524-29.

(47) Grover S, Srivastava A, Lee R, Tewari A K, Te A E. Role of inflammation in bladder function and interstitial cystitis. Ther Adv Urol 2011; 3; 19-33.

(48) Frangogiannis N G, Smith C W, Entman M L. The inflammatory response in myocardial infarction. Cardiovasc Res 2002; 53; 31-47.

(49) Tang T T, Yuan J, Zhu Z F, Zhang W C, Xiao H, Xia N, et al. Regulatory T cells ameliorate cardiac remodeling after myocardial infarction. Basic Res Cardiol 212; 107; 232-48.

(50) Inoue M, Arikawa T, Chen Y H, Moriwaki Y, Price M, Brown M, et al. T cells down-regulate macrophage TNF production by IRAK1-mediated IL-10 expression and control innate hyperinflammation. Proc Natl Acad Sci USA. Mar. 21, 2014 Epub ahead of print

(51) Deng G M, Beltran J, Chen C, Terhorst C, Tsokos G C. T cell CD3ζ deficiency enables multiorgan tissue inflammation. J Immunol 2013; 191; 3563-567.

(52) Azouz A, Razzaque M S, El-Hallak M, Taguchi T. Immunoinflammatory responses and fibrogenesis. Med Electron Microsc 2004; 37; 141-48.

(53) Park J E, Barbul A. Understanding of the role of immune regulation in wound healing. Am J Surg 2004; 187; 11S-16S.

(54) Calderon V E, Valbuena G, Goez Y, Judy B M, Huante M B, Sutjita P, et al. A humanized mouse model of tuberculosis. PLoS One 2013; 8; e63331.

(55) Kim J, Chae C. Expression of monocyte chemoattractant protein-1 and macrophage inflammatory protein-1 in porcine circovirus 2-induced granulomatous inflammation. J Comp Pathol. 2004; 131; 121-26.

(56) Lekstrom-Himes J A, Kuhns D B, Alvord W G, Gallin J I. Inhibition of human neutrophil IL-8 production by hydrogen peroxide and dysregulation in chronic granulomatous disease. J Immunol 2005; 174; 411-17.

(57) Hamid R, Robertson W G, Woodhouse C R. Comparison of biochemistry and diet in patients with enterocystoplasty who do and do not form stones. BJU Int 2008; 101; 1427-32.

(58) Bladder Stones: Medline Plus. National Library of Medicine. nlm.nih.gov/medlineplus/ency/article/001275.htm

The invention claimed is:

1. A peptide amphiphile comprising:
a hydrophobic non-peptidic segment comprising an acyl chain of 16 carbons in length covalently attached to a peptide of VVVAAAEEEMQMKKVLDS (SEQ ID NO:1) or VVVAAAEEEHDMNKVLDL (SEQ ID NO:2).

2. A nanofiber comprising the peptide amphiphile of claim 1.

3. A method of promoting tissue regeneration in a subject comprising administering the peptide amphiphile of claim 1 to the subject.

4. The method of claim 3, wherein inflammation is modulated in the subject.

5. The method of claim 4, wherein inflammation is reduced in the subject.

* * * * *